US011887621B2

(12) United States Patent
Schultz et al.

(10) Patent No.: US 11,887,621 B2
(45) Date of Patent: Jan. 30, 2024

(54) BIOMETRIC SENSOR DEVICE FOR DIGITAL QUANTITATIVE PHENOTYPING

(71) Applicant: The Children's Hospital of Philadelphia, Philadelphia, PA (US)

(72) Inventors: Robert Schultz, Swarthmore, PA (US); G. Keith Bartley, Malvern, PA (US); Evangelos Sariyanidi, Philadelphia, PA (US); Julia Parish-Morris, Ft. Washington, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 859 days.

(21) Appl. No.: 16/964,800

(22) PCT Filed: Jan. 25, 2019

(86) PCT No.: PCT/US2019/015178
§ 371 (c)(1),
(2) Date: Jul. 24, 2020

(87) PCT Pub. No.: WO2019/147955
PCT Pub. Date: Aug. 1, 2019

(65) Prior Publication Data
US 2021/0052205 A1      Feb. 25, 2021

Related U.S. Application Data

(60) Provisional application No. 62/621,762, filed on Jan. 25, 2018.

(51) Int. Cl.
*G10L 25/48*      (2013.01)
*A61B 5/00*      (2006.01)
(Continued)

(52) U.S. Cl.
CPC .............. *G10L 25/48* (2013.01); *A61B 5/002* (2013.01); *A61B 5/0077* (2013.01); *A61B 5/167* (2013.01);
(Continued)

(58) Field of Classification Search
CPC ... G06F 21/32; G06F 21/6245; H04L 9/3231; H04L 2209/42; G06V 10/454; H06F 21/32
See application file for complete search history.

(56) References Cited

U.S. PATENT DOCUMENTS 8,131,026 B2 * 3/2012 Benkley .............. G06F 3/03547
340/5.83
8,165,355 B2 * 4/2012 Benkley .............. G06F 3/03547
345/156
(Continued)

FOREIGN PATENT DOCUMENTS

WO      2017039704 A1      3/2017

OTHER PUBLICATIONS

Landowska, "Emotion Monitor-Concept Construction and Lessons Learned," Proceedings of the Federated Conference on Computer Science and Information Systems, ACSIS, vol. 5, pp. 75-80.
(Continued)

*Primary Examiner* — Yosef Kassa
(74) *Attorney, Agent, or Firm* — RatnerPrestia

(57) ABSTRACT

A biometric sensor device system including a biometric sensor device, and a prediction computer. The biometric sensor device includes at least one camera, and a biometric sensor device processor configured to record a time synchronized communicative interaction between participants, by controlling at least one camera to record the participants over a time period, and transfer the recorded communicative interaction to the prediction computer. The prediction com-
(Continued)

puter including a prediction computer processor configured to extract, from the recorded communicative interaction, a physical characteristic of each of the participants over the time period, compare the physical characteristic of at least one of the participants with the physical characteristic of at least another one of the participants over the time period, and classify or score at least one of the participants according to a predetermined classification or dimensional scoring scheme based on the comparison.

20 Claims, 21 Drawing Sheets

(51) Int. Cl.
| | |
|---|---|
| *A61B 5/16* | (2006.01) |
| *G10L 25/66* | (2013.01) |
| *G06V 20/40* | (2022.01) |
| *G06V 40/20* | (2022.01) |
| *G06V 40/16* | (2022.01) |
| *G06F 18/213* | (2023.01) |
| *G06F 18/2411* | (2023.01) |
| *G06V 10/764* | (2022.01) |
| *G06V 10/771* | (2022.01) |
| *G06V 10/77* | (2022.01) |

(52) U.S. Cl.
CPC .......... *A61B 5/4803* (2013.01); *A61B 5/7246* (2013.01); *A61B 5/7264* (2013.01); *G06F 18/213* (2023.01); *G06F 18/2411* (2023.01); *G06V 10/764* (2022.01); *G06V 10/771* (2022.01); *G06V 10/7715* (2022.01); *G06V 20/41* (2022.01); *G06V 40/176* (2022.01); *G06V 40/20* (2022.01); *G10L 25/66* (2013.01); *A61B 2562/16* (2013.01)

(56) References Cited

U.S. PATENT DOCUMENTS

| | | | |
|---|---|---|---|
| 8,447,077 B2* | 5/2013 | Benkley | ................ G06T 7/248 382/107 |
| 8,659,433 B2* | 2/2014 | Petrou | .................... G06F 1/163 340/573.7 |
| 9,239,944 B2* | 1/2016 | Abe | ..................... G06V 10/993 |
| 9,721,137 B2* | 8/2017 | Benkley | ............. G06V 40/1335 |
| 10,419,221 B1* | 9/2019 | Streit | ..................... G06F 21/32 |
| 2017/0277844 A1 | 9/2017 | Apte et al. | |

OTHER PUBLICATIONS

International Search Report and Written Opinion issued in PCT/US2019/015178, dated Mar. 27, 2019, 7 pages.

International Preliminary Report on Patentability and Written Opinion for International Application No. PCT/US2019/015178, dated Jul. 28, 2020, 7 pages.

\* cited by examiner

234/236

US 11,887,621 B2

BIOMETRIC SENSOR DEVICE FOR DIGITAL QUANTITATIVE PHENOTYPING

CROSS REFERENCE TO RELATED APPLICATIONS

This application is a U.S. National Phase Application of PCT International Application No. PCT/US2019/015178, filed Jan. 25, 2019, which claims benefit of priority from U.S. Provisional Application No. 62/621,762, filed Jan. 25, 2018. The contents of these applications are incorporated herein by reference.

FIELD

The subject matter disclosed herein relates to devices and methods for digital quantitative phenotyping.

BACKGROUND

Experts in various industries have long used physical characteristics and behavior of humans to perform classifications and predictions. For example, medical doctors observe the physical characteristics and behavior of a patient in order to make a diagnosis of a neurological disorder. Such qualitative phenotyping systems, however, may be inaccurate due to high dependency on various factors including the experience of the doctor, which often leads to prediction inaccuracies (e.g., false positives or false negatives).

SUMMARY

An embodiment includes a biometric sensor device system comprising a biometric sensor device, and a prediction computer. The biometric sensor device includes at least one camera, and a biometric sensor device processor configured to record a time synchronized communicative interaction between participants, by controlling at least one camera to record the participants over a time period, and transfer the recorded communicative interaction to the prediction computer. The prediction computer including a prediction computer processor configured to extract, from the recorded communicative interaction, a physical characteristic of each of the participants over the time period, compare, the physical characteristic of at least one of the participants with the physical characteristic of at least another one of the participants over the time period, and classify or score at least one of the participants according to a predetermined classification or dimensional scoring scheme based on the comparison.

A biometric sensor device comprising at least one camera, and a processor configured to record a time synchronized communicative interaction between participants, by controlling the at least one camera to record the participants over a time period, extract, from the recorded communicative interaction, a physical characteristic of each of the participants over the time period, compare, the physical characteristic of at least one of the participants with the physical characteristic of at least another one of the participants over the time period, and classify or score at least one of the participants according to a predetermined classification or dimensional scoring scheme based on the comparison.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1A:
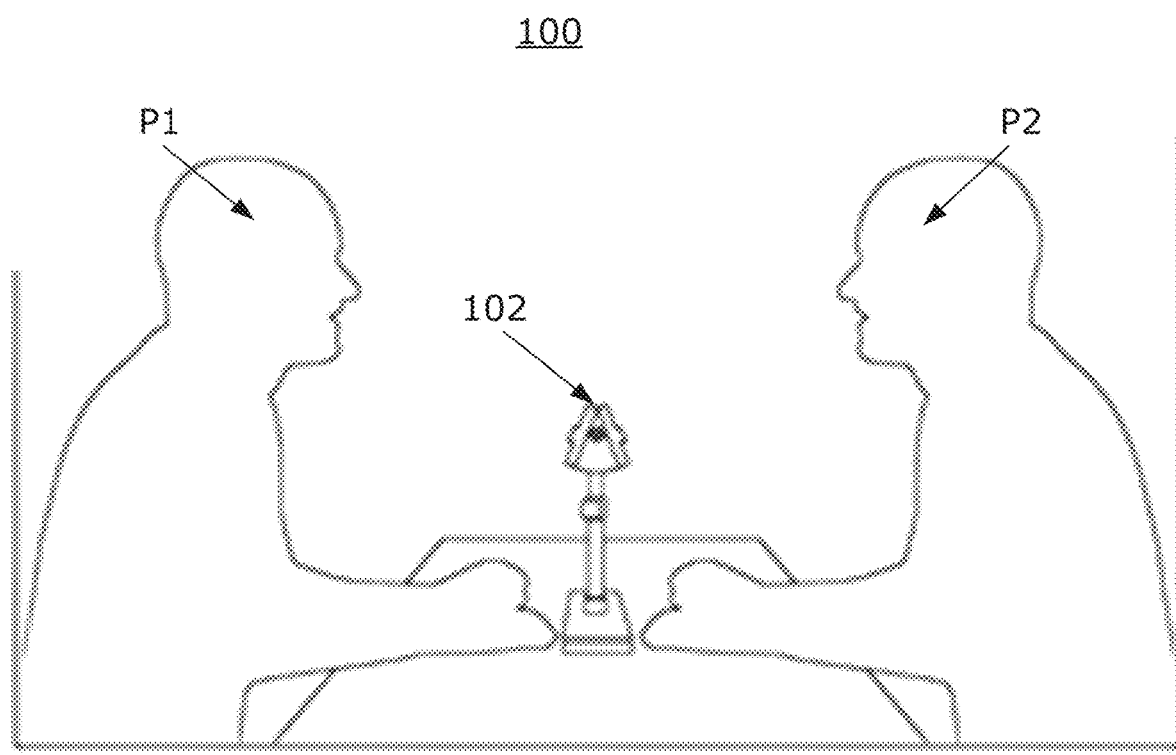
FIG. 1A is a view of a communicative (e.g., dyadic) interaction between two participants where a biometric sensor device is positioned on a tabletop between the participants, according to an aspect of the disclosure.
Figure 1B:
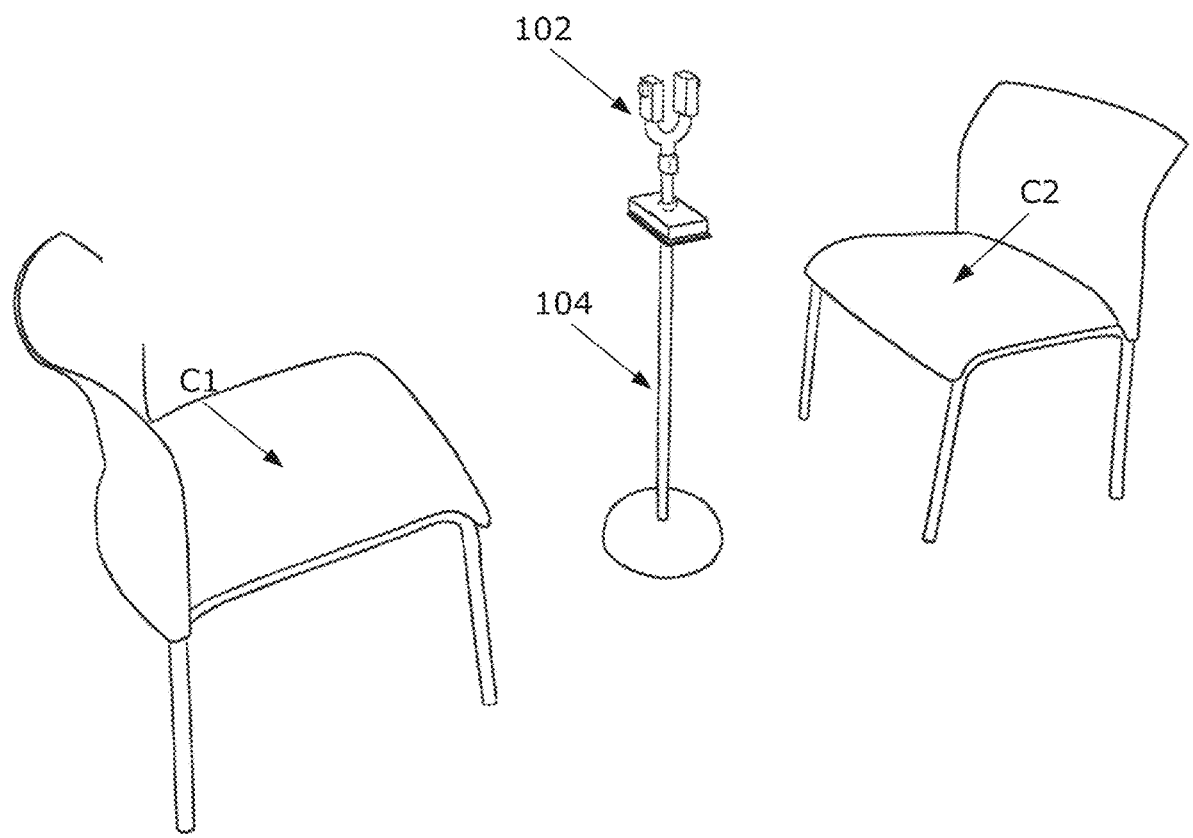
FIG. 1B is a view of the biometric sensor device in FIG. 1A positioned on the ground between the participants, according to an aspect of the disclosure.

FIG. 1A is a view 100 of a communicative (e.g., dyadic) interaction between two participants (P1 and P2) recorded by biometric sensor device 102 positioned on a table between the participants. FIG. 1B is a view 103 of the communicative (e.g., dyadic) interaction recorded by biometric sensor device 102 having an adjustable stand 104 (e.g., telescopic pole) placed on the ground between chairs C1 and C2 of the two participants (not shown). Although FIGS. 1A and 1B show views of biometric sensor device 102 configured to record a dyadic interaction between two participants, it is noted that it could be set up to record other types of communicative interactions (e.g., activity and interactions between more than two participants) as well as solitary activity (e.g., activity of a single participant). For explanation purposes, the recording of the communicative interactions or of the solitary activity is referred to as a recorded "session."

Sessions of communicative interactions or solitary activity are beneficial, because they provide information (e.g., neurological or psychological) about the participant(s) involved. Third parties (e.g., researchers, doctors, match makers, etc.) may use this information to classify the participant(s) into various classifications (e.g., classifying the participant as being a member of a group) and/or to predict rankings/scores (e.g., ranking the classified participant to a level within the group such as mild/severe such as scoring the classified participant on a scale from 0-10, etc.). This classification/scoring procedure is a form of quantitative phenotyping also known as "digital quantitative phenotyping."

A phenotype is an observable expression of an underlying condition. Digital quantitative phenotyping involves precisely measuring the observable expression in a framework that quantifies the observations. Digital quantitative phenotyping may be beneficial in many applications. For example, in the medical industry, a computer (e.g., internal or external to the biometric sensor device) may analyze a session of the dyadic interaction shown in FIG. 1A or a session of solitary activity (not shown), and classify one or more of the participant(s) (e.g., the subject) as testing positive for a neurological disorder such as autism spectrum disorder (ASD) or a psychological disorder such as depression. The computer may also score the participant(s) (e.g., grade the subject(s) as having mild, moderate, or severe ASD, or on a continuous quantitative scale with infinitely fine gradations). When applied at multiple time points, such scoring can assess whether an intervention or treatment for a disorder or condition is having beneficial or other effects. In another example, in the matchmaking and/or counseling industries, the computer may use the session shown in FIG. 1A to determine if the participants are romantically compatible with one another, or to assess deterioration of progress in the quality of a romantic relationship, or to assess a specific intervention (e.g., such as marriage counseling). In yet another example, in the human resources industry, the computer may use the session shown in FIG. 1A to determine job compatibility. For example, the computer may determine if a participant (e.g. job interviewee) would be good fit for a particular job position, or assess the participant for placement in an alternative job position. This may be particularly useful for evaluating participants for job positions (e.g. management, sales, nursing, etc.) where employees must have good communication skills, and in scenarios where the participant (e.g. interviewee) is communicating remotely (e.g. video conference) with the employer. In a similar manner, the computer can assess deterioration or improvement over time of a neurological or psychological condition as the result of an intervention or as a result of the normal life course of the condition. Many neurological and psychological conditions, and personal and interpersonal traits are understood from descriptions of what the person can do well and cannot do well, or does too much or too little. The biometric sensor device is designed to accurately measure all of these behaviors and attributes, which represent underlying biological condition(s) or capacity(s).

Biometric Sensor Device Hardware

Biometric sensor device 102 is a tool for capturing a session between two (i.e., dyadic) or more than two participants. Biometric sensor device 102 may also be used for capturing a session of solitary activity of a single participant. During the session, biometric sensor device 102 captures physical characteristics of the participant(s). Among others, these may include gross and fine motor movements, facial expressions, speech/utterances, heart rate, heart rate variability and other dynamic processes such as nonverbal facial signals, arm gestures and communicative body postures inviting approach, approval, disapproval, etc.

Figure 2A:
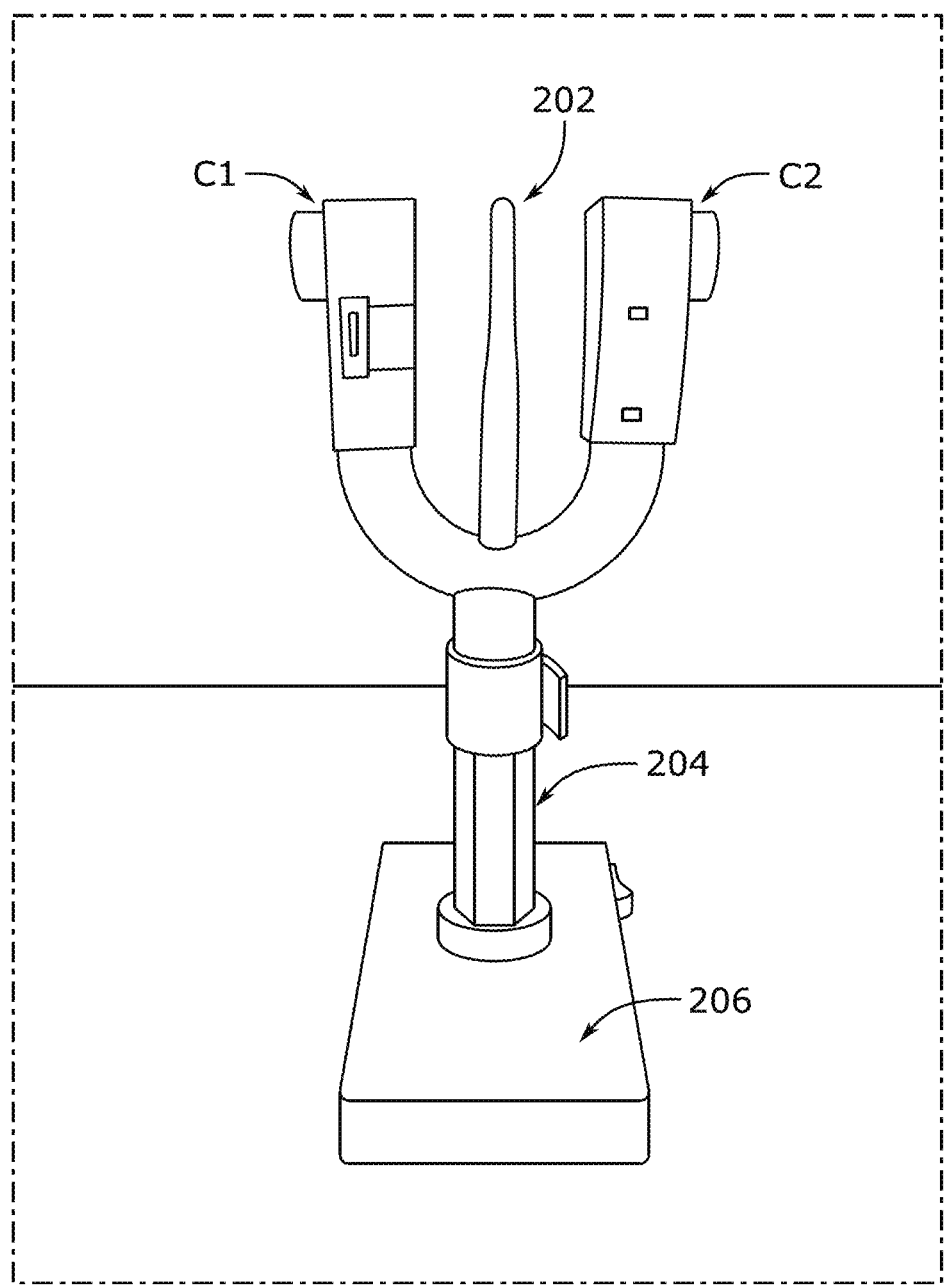
FIG. 2A is a side view of the biometric sensor device, according to an aspect of the disclosure.
Figure 3A:
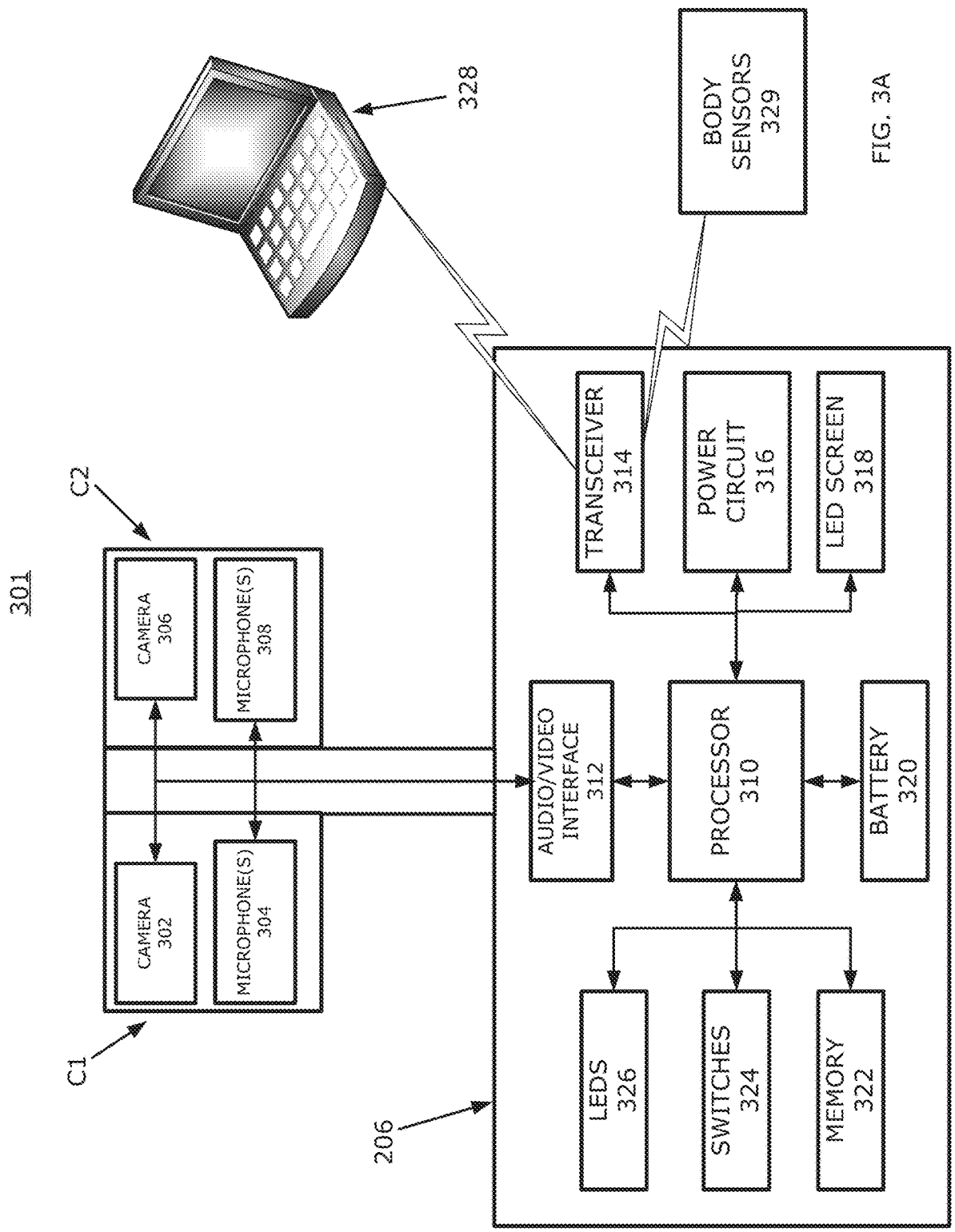
FIG. 3A is a hardware block diagram of the biometric sensor device in FIG. 2A, according to an aspect of the disclosure.

FIG. 2A is a side view 201 of a biometric sensor device such as the one shown in FIGS. 1A and 1B. In this example, the biometric sensor device (e.g., molded from plastic) includes a radio frequency (RF) antenna 202 and two cameras C1 and C2 mounted to base 206 via support post 204. Antenna 202 wirelessly transmits and receives data to and from other wireless biometric sensors, the base station, and external computer(s) (e.g., personal computer, cloud computers, etc.). Cameras C1 and C2, and 2 or more microphones (e.g., participant-facing microphones 304/308 as shown in FIG. 3A) capture images, video, and/or audio of participants P1 and P2 during the session shown in FIG. 1A. Base 206 houses electronics such as an internal computer (not shown) that controls the functionality of the biometric sensor device to record the session. Although not shown in FIG. 2A, electrical wires are also routed from the computer in base 206 to cameras C1 and C2, antenna 202 and participant-facing microphones (not shown).

Figure 2B:
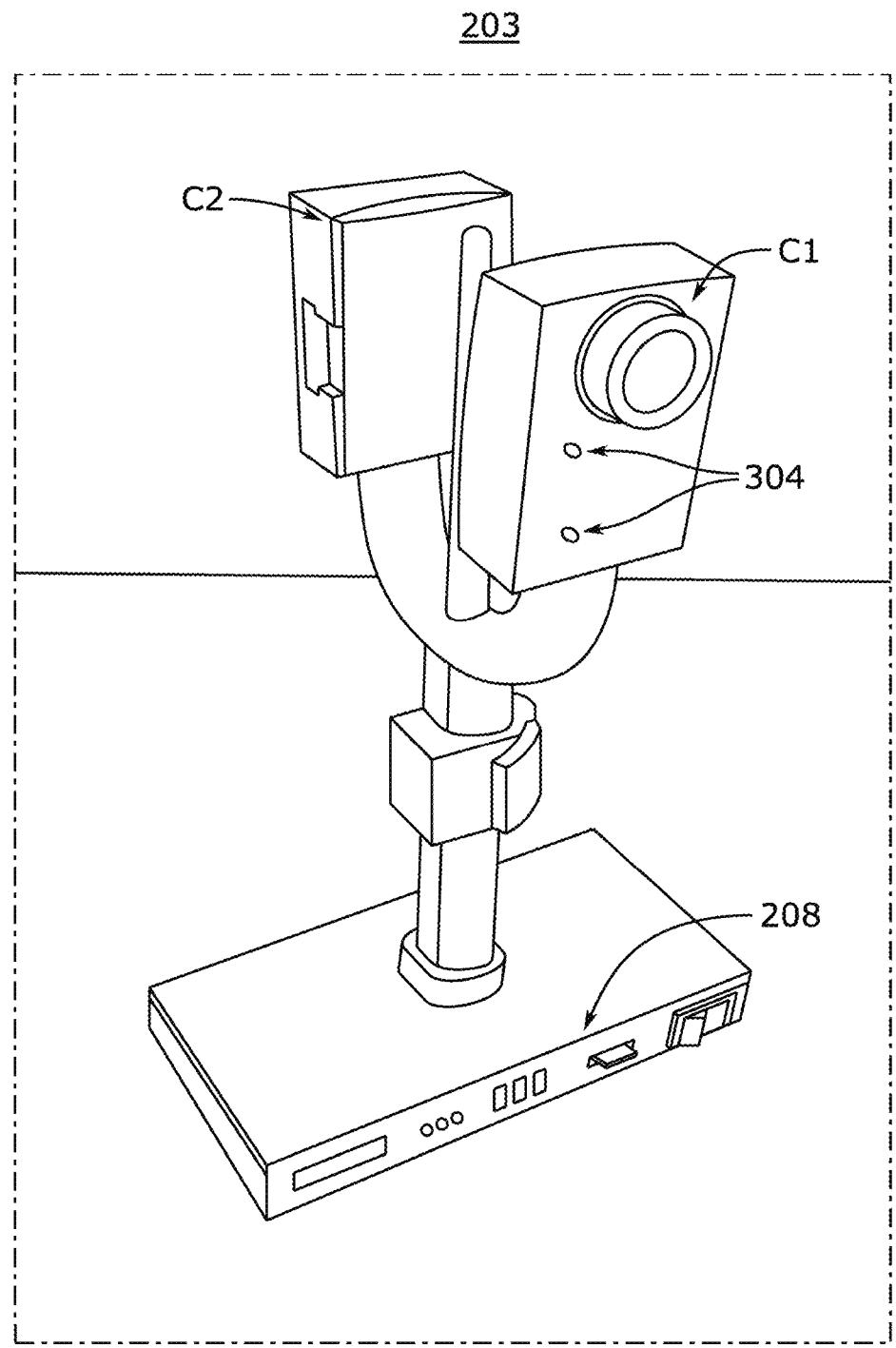
FIG. 2B is a profile view of the biometric sensor device in FIG. 2A, according to an aspect of the disclosure.

FIG. 2B is a perspective view 203 of the biometric sensor device in FIG. 2A showing further details of base 206 and the placement of two participant-facing microphones 304. In this example, the two participant-facing microphones 304 are configured on one branch of the biometric sensor device to capture audio from participant(s) being recorded by camera C1. Although not shown, two more participant-facing microphones 308 are configured on the other branch of the biometric sensor device to capture audio from participant(s) being recorded by camera C2. The device might also have more than two cameras, not shown, facing multiple different directions in order to capture interactions of groups of people (e.g. more than two people).

Figure 2C:
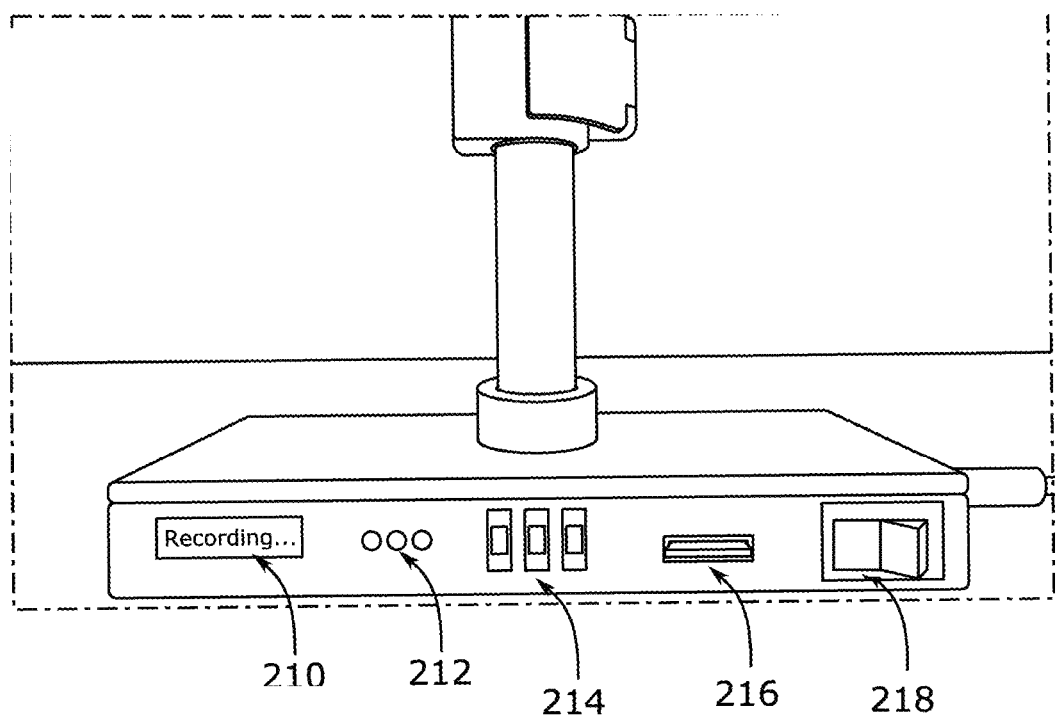
FIG. 2C is a close-up view of a base of the biometric sensor device in FIG. 2A, according to an aspect of the disclosure.

In this example, base 206 includes various external electronic components on front panel 208. FIG. 2C is close-up view 205 of the external electronic components on front panel 208 in FIG. 2A. In this example, base 206 includes display 210 such as a liquid crystal display (LCD), light emitting diode (LED) display or the like. In this example, base 206 also includes LED indicator lights 212, function switches 214, memory card slot 216 and power switch 218.

In one example, to record a session, the operator (e.g., one of the participants in the session or a third party) would turn on power switch 218 and engage one or more of function switches 214 to begin recording. Indicator lights 212 and display 210 indicate that the biometric sensor device is recording the session between the participants. The biometric sensor device may then either analyze the recorded data and output a prediction (e.g., a classification/scoring that can be used for decisions) on display 210, store the data in memory card 216, or transmit the data via antenna 202 to an external computer (e.g., personal computer, cloud computers, etc.) to perform the prediction (e.g., a classification/scoring).

Figure 2D:
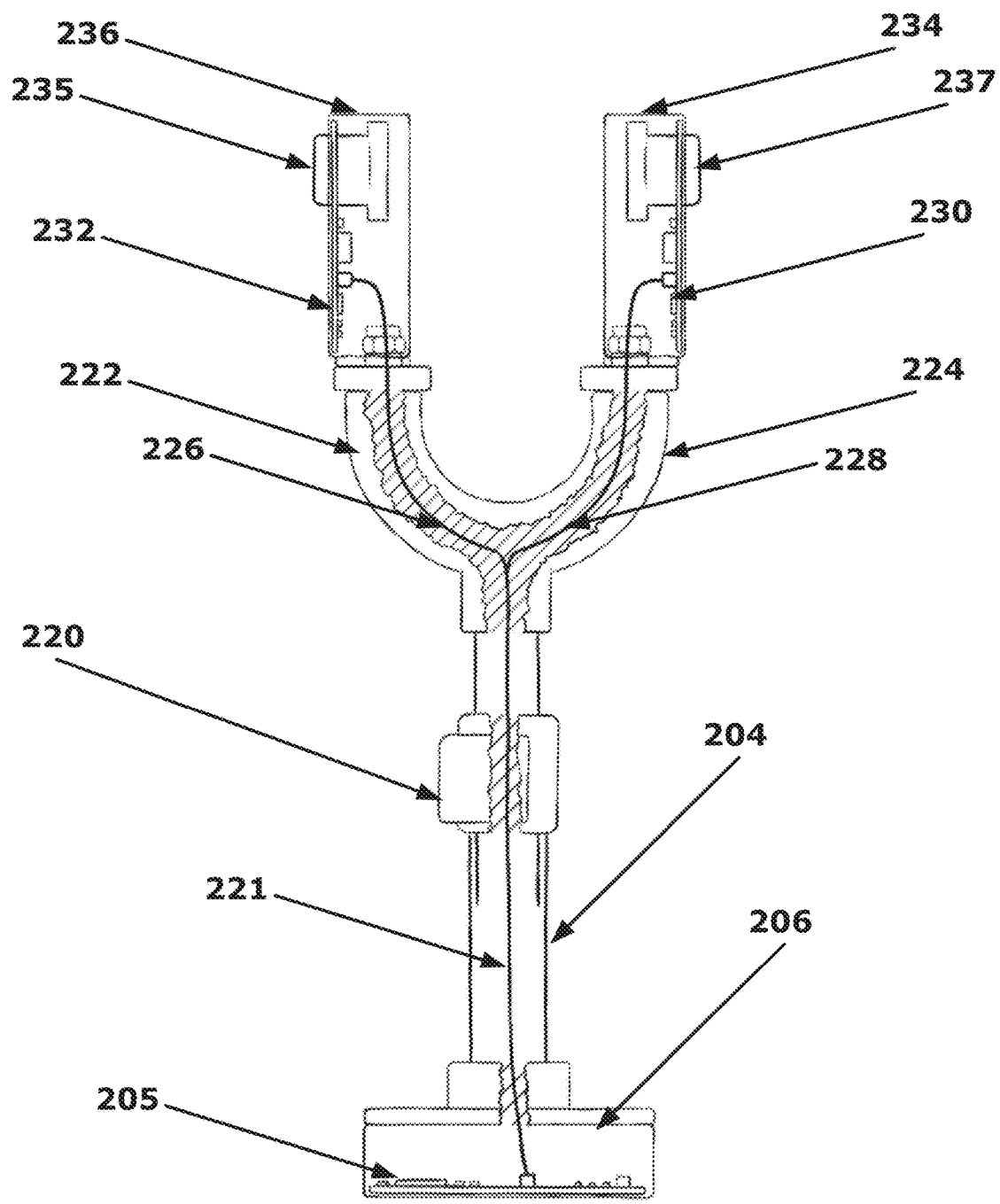
FIG. 2D is a cutaway side view of the biometric sensor device in FIG. 2A showing wires routed from the base to the camera housing, according to an aspect of the disclosure.

FIG. 2D is another side view of the biometric sensor device in FIG. 2A with internal wires 221, 226 and 228 shown. As described above, the biometric sensor device includes base 206 which houses electronic components 205 (e.g., computer) and hollow support post 204. In addition, the biometric sensor device includes adjustable collar 220 that connects to hollow left branch 222 supporting left camera housing 236, and connects to hollow right branch 224 supporting right camera housing 234. In one example, collar 220 is loosened to allow the height of the cameras to be adjusted, and then tightened to fix the height of the cameras.

As shown in this cutaway view, wires 221, 226 and 228 are routed from electronics 205 in base 206 to electronics 232 and camera 235 in left camera housing 236 and electronics 230 and camera 237 in right camera housing 234 respectively. These wires connect electronics 205 in base 206 with electronic circuits 232 and 230 in the left camera housing 236 and right camera housing 234 respectively. These wires carry power as well as data signals (e.g., control signals, video signals, audio signals, etc.) between the controller, cameras, microphones and other electronic components. Although FIG. 2D appears to show wires 221, 226 and 228 as single wires, it is noted that in practice, these wires could represent multiple wires (e.g., separate control wires, power wires, etc.) to support the operation of the biometric sensor device.

As described above, multiple wires are routed through the support post, the branches, and into the camera housings which are moveable (e.g., rotatable) relative to the base. In order to avoid impeding the movement of the camera housings, the mechanical connection point between the branches and camera housings are designed to allow for free movement.

Figure 2E:
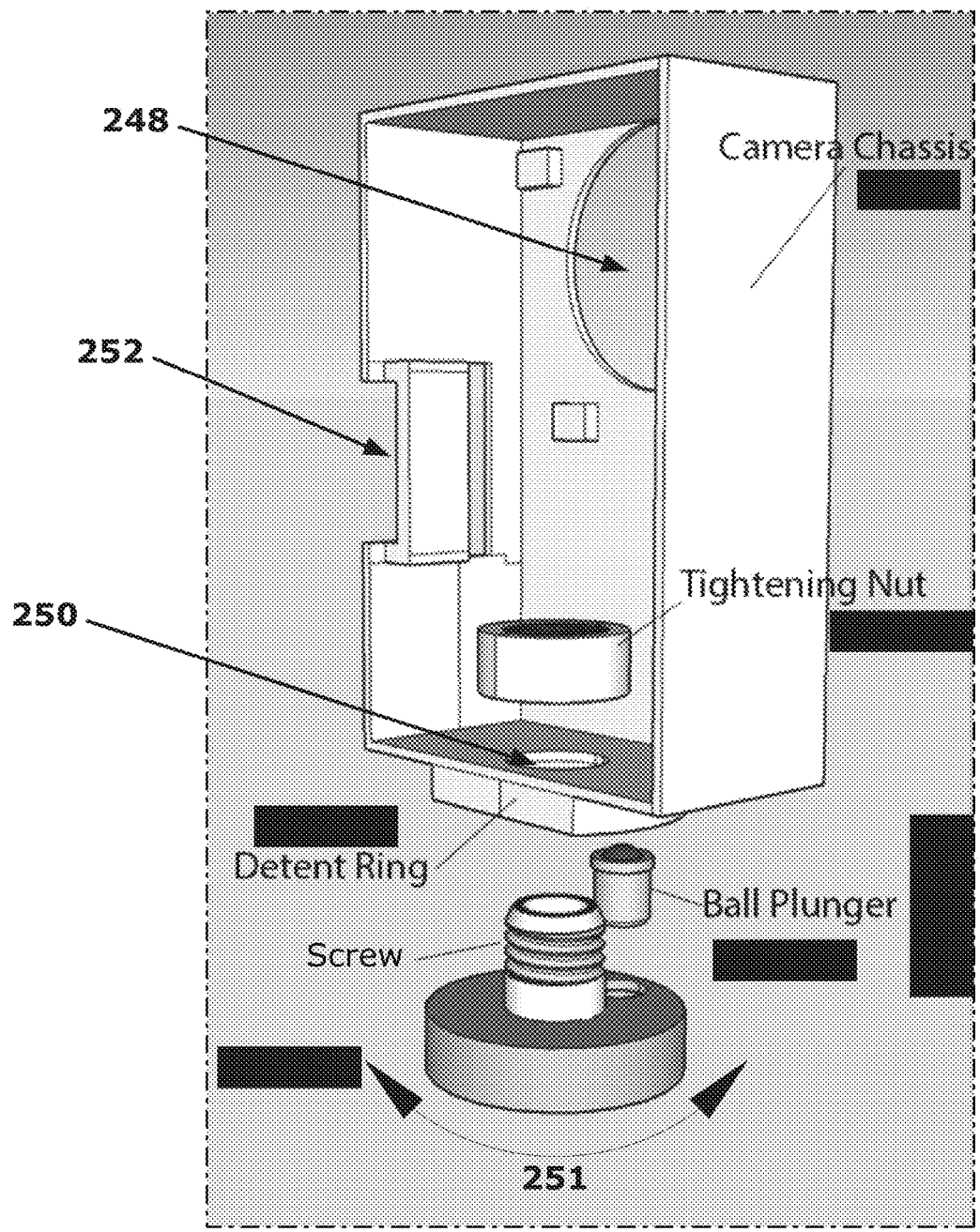
FIG. 2E is a profile view of the camera housing of the biometric sensor device in FIG. 2A, according to an aspect of the disclosure.

FIG. 2E shows an example of a camera housing of the biometric sensor device in FIG. 2A. The camera housing includes camera chassis 238 (e.g., plastic box) that houses the electronic components (e.g., camera, microphone, etc.). The camera chassis 238 includes a wire hole 250 that allows wires to enter/exit the housing (see FIG. 2D), and camera hole 248 that allows the camera to be mounted within the housing. In addition, camera chassis 238 also includes a latch 252 that receives a cover plate (not shown) for sealing the back side of the housing.

In this example, the connection point between the housing and the branch includes detent ring 240, hollow shoulder screw 242 and ball plunger 244. Hollow shoulder screw 242 is inserted into hole 250 and held in place by tightening nut 246 such that ball plunger 244 is sandwiched between the hollow shoulder screw and the camera chassis (e.g., the plunger is inserted into the hollow shoulder screw and positioned such that the ball presses against the surface of the detent ring). Ball plunger 244 is a device (e.g., spring loaded device) that applies tension between the hollow shoulder screw and the camera chassis, while still allowing the camera chassis to rotate around the screw along a direction indicated by arrow 251. For example, when assembled, the free rolling ball of ball plunger 244 contacts the surface of detent ring 250 at the bottom of the chassis, while the fixed portion of the ball plunger is inserted into the hollow shoulder screw. This allows chassis 238 to rotate around the screw such that the ball of the ball plunger rides along the surface of detent ring 250. Essentially, hollow shoulder screw 242 holds the chassis in place on a rotation axis, while ball plunger 244 allows the chassis to rotate around the axis in direction 251.

Figure 2F:
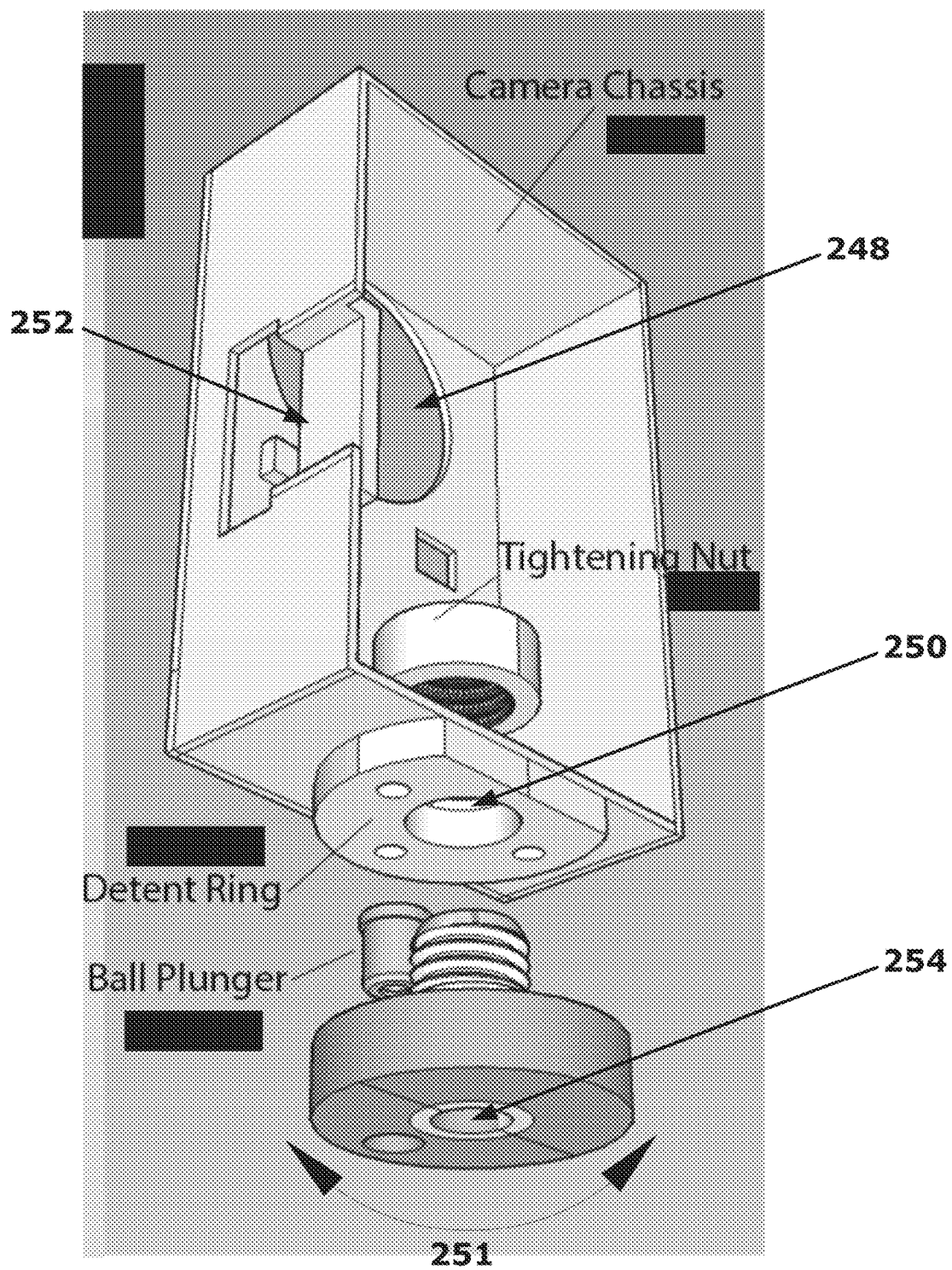
FIG. 2F is another profile view of the camera housing of the biometric sensor device in FIG. 2A, according to an aspect of the disclosure.

FIG. 2F is another profile view of the camera housing in FIG. 2E. The view in FIG. 2F shows the bottom portion of chassis 238 that includes detent ring 240. This view is also beneficial to understand how wires are routed into the camera housing through hole 250.

Although not shown, branches 222 and 224 of the biometric sensor device may be coupled to the base of hollow shoulder screw 242 such that screw hole 254 is exposed to the hollow shaft of the branch. This allows wires (see FIG. 2D) to be routed through the branches 222 and 224 of the device, routed through hole 254, routed through the hollow portion of screw 242 and routed through hole 250 into camera chassis 238. The wires may then be connected (not shown) via connectors, soldered or the like to electronic components (e.g., a circuit board for the camera and microphones) that are also mounted inside chassis 238. The same configuration would be used for both the left and right camera housings (e.g., both branches).

The biometric sensor device includes electrical components in both its base and its camera housings that are connected to each other via wires. FIG. 3A is an example hardware block diagram 301 showing details of the internal components of the biometric sensor device in FIG. 2A. Base 206 includes a processor 310 that controls various electrical components of the biometric sensor device. These electrical components include cameras 302/306 for recording video of the participants, microphones 304/308 for recording audio of the participants, and audio/video interface 312 for interfacing processor 310 to the cameras and microphones. Although FIG. 3A shows branches having two cameras and two microphones, it is noted that other configurations are possible. For example, the biometric sensor device may include a single branch with single camera and a single microphone. In another example, the biometric sensor device may include more than two branches, more than two cameras, and more than two microphones. Such hardware configurations may be beneficial in certain communicative (e.g., group) interactions or to observe solitary activity of a single participant.

In the example in FIG. 3A, the electrical components of the biometric sensor device also include transceiver 314 (e.g., Bluetooth) for wirelessly communicating with external computer(s) (e.g., cloud computers) 328 and wireless body sensor(s) 329 (e.g., ECG sensors, Accelerometers, Gyroscopes, etc.), power circuit 316 for managing voltage (e.g., line or battery voltage) to power the biometric sensor device, LED screen 318 for displaying information to the participant(s) or to the operator, power source 320 for powering the electronic components of the biometric sensor device, memory 322 (e.g., SD card) for storing the recorded session, function switches 324 for controlling the functionality (e.g., recording) of the biometric sensor device, and indicator LEDs 326 to indicate the operational mode of the biometric sensor device.

The biometric sensor device is a custom-engineered tool having various measurement channels that enable synchronized measurement of biometric data including but not limited to high resolution video (e.g., facial movements, gestures, head, body and limb movements), audio (e.g., lexical and acoustic properties of speech), and body sensors 329 for measuring limb accelerometry/gyroscopy (e.g., participant wearables) and electrocardiography (ECG) heart rate variability (e.g., an index of anxiety or arousal). This time synchronization occurs between multiple sensor channels for the same participant and between channels for different participants.

Measured facial movements can, with the proper lighting conditions, include small movements such as pupil dilation and constriction as behavioral measurements. Thus, the biometric sensor device is also capable of video pupillometry (e.g., as a measure of arousal and cognition, etc.). The device can also be used to record the behavior from just one person alone, including pupillometry, heart rate measures, facial and body movements, speech, etc. In one example, this person could be completing an activity (e.g., on a computer or with papers or other materials). Scoring and classification can be based on input from this one person alone. The biometric sensor device presents an all-in-one digital quantitative phenotyping tool allowing detailed and comprehensive measurement of various dimensions of observable human behavior, cognition and psychological arousal. Because data collection through each channel (e.g., video, audio, accelerometry/gyroscopy, ECG, etc.) can be time synchronized, the data is ready for analytic pipelines and statistical modeling by the biometric sensor device or by another computer device. Statistical modeling can use the data from all of the channels together, a select subset of the channels or just one of the channels.

In one example, the biometric sensor device includes two high temporal-spatial resolution cameras with multiple directional microphones, which are tailored for blind source separation. In this example, these cameras each capture video with a 160 degrees field of view, and are capable of recording hours of continuous high spatial and temporal resolution video (e.g., 1920×1440 at 60 frames/second, 150 degree field of view). By reducing the temporal resolution to 30 FPS, spatial resolution can be increased (e.g., 3840× 2160) without increasing storage demands.

As described above, the system may include wireless wearable devices (not shown) worn by one or more of the participants that communicate additional biometric data to the biometric sensor device computer via wireless protocol such as Bluetooth. The wearable may include hardware for ECG measurement of heart rate and heart rate variability as an index of arousal/anxiety, and limb accelerometry and gyroscopy for assessing movement (e.g., for gestures, repetitive behaviors of the participants, etc.). The wearable and ECG devices described above are capable of recording hours of data without interruption at a very high sampling rate (e.g., 1000 times per second).

Figure 3B:
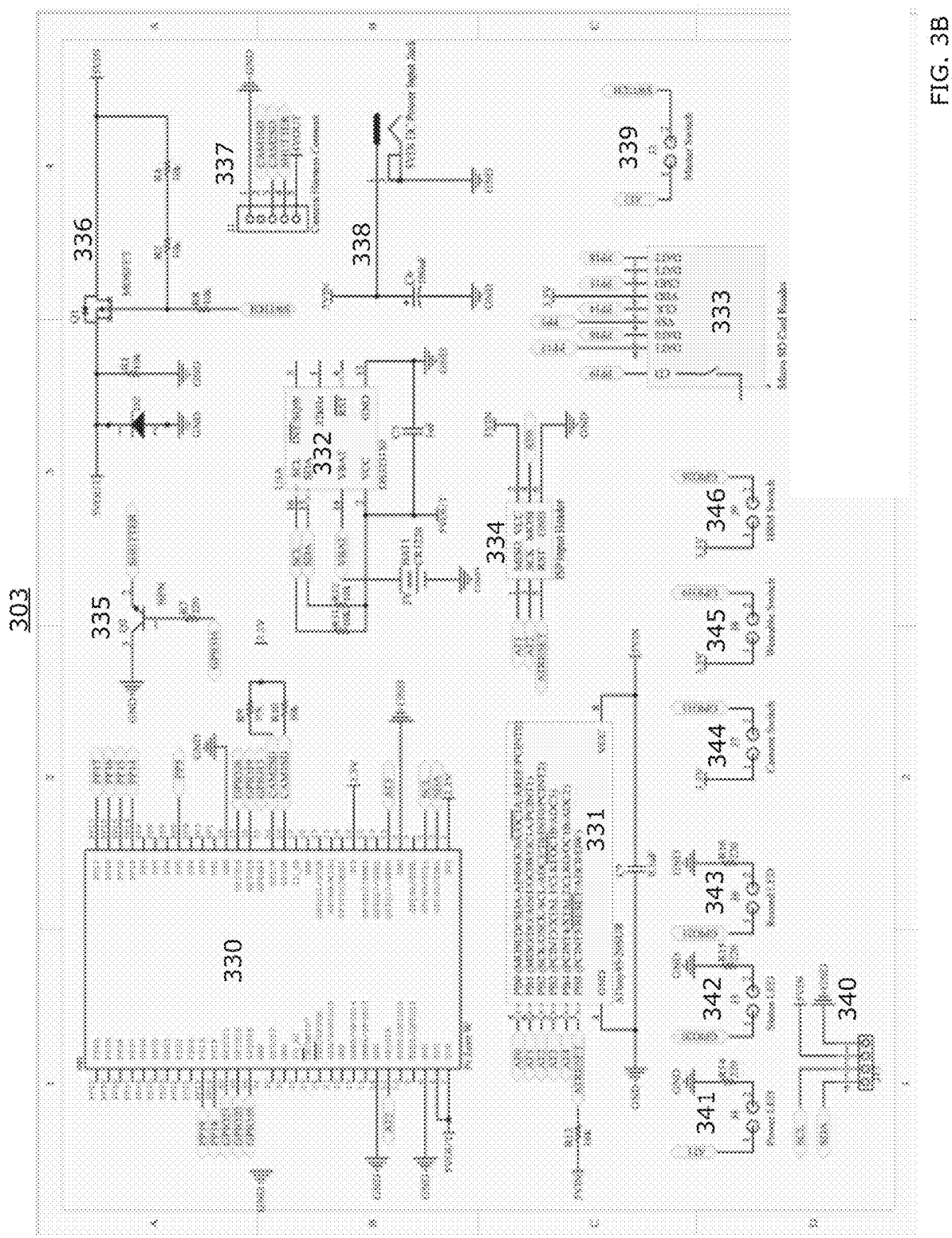
FIG. 3B is a schematic diagram of the electronics of the biometric sensor device base in FIG. 2A, according to an aspect of the disclosure.

FIG. 3B is an example schematic diagram 303 of the biometric sensor device base 206. In one example, biometric sensor device base 206 includes central processing unit (CPU) 330 for controlling the biometric sensor device electronic components and possibly for analyzing the captured data. In this example, biometric sensor device base 206 also includes AT 85-20SUR 331 microcontroller for coordinating power on/off procedures between all devices in response to outside input from a user, and DS3231S Real Time Clock 332 for accurately tracking timestamps for all received data and for maintaining a reference point for date and time independent of any external power source through use of an onboard battery (not shown).

In one example, biometric sensor device base 206 includes micro-secure digital (SD) card reader 333 for accepting external memory cards, in-system programming (ISP) input header 334 for programming the device, shutter switch circuits 335 and 336 for controlling the camera shutters, camera harness connector 337 for connecting CPU 330 to the cameras, power input jack circuit 338 for receiving input power, master switch 339 for controlling flow of the input power, terminal 340 for coupling to the power wires, power LED 341 for indicating the power status of the biometric sensor device, status LED 342 for indicating functional status of the biometric sensor device, record LED 343 for indicating recording status of the biometric sensor device, camera switch 344 for controlling the operation of the cameras, wearable switch 345 for controlling the operation of the wearables, and HRM switch 346.

Figure 3C:
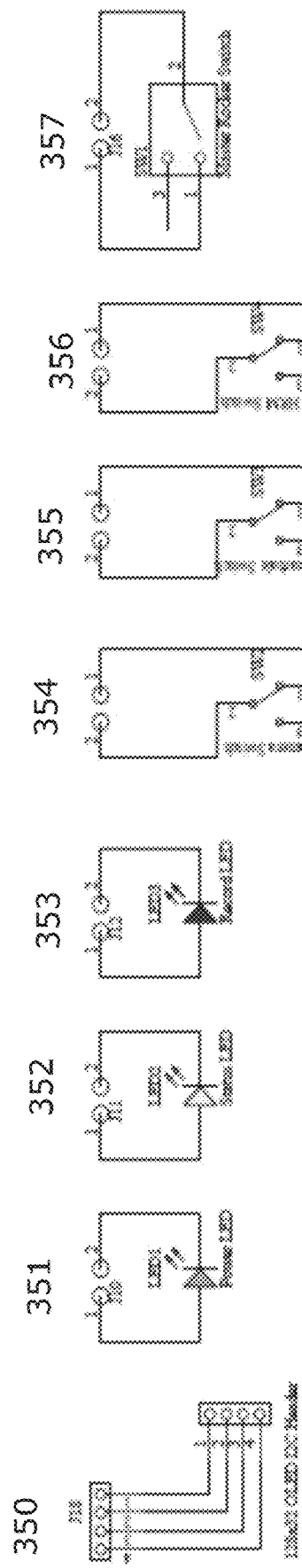
FIG. 3C is a schematic diagram of electronics of a front panel of the biometric sensor device in FIG. 2A, according to an aspect of the disclosure.

FIG. 3C is another schematic diagram 305 showing the electronics of a front panel of the biometric sensor device (e.g., the devices accessible by the operator). The front panel in this example includes organic LED (OLED) header 350 for connecting to the LED display 210. Also included are power LED 351, status LED 352, record LED 353, camera switch 354, wearable switch 355, HRM switch 356 and master rocker switch 357. The functionality of these components is already described with reference to FIGS. 2C and 3B above.

Figure 3D:
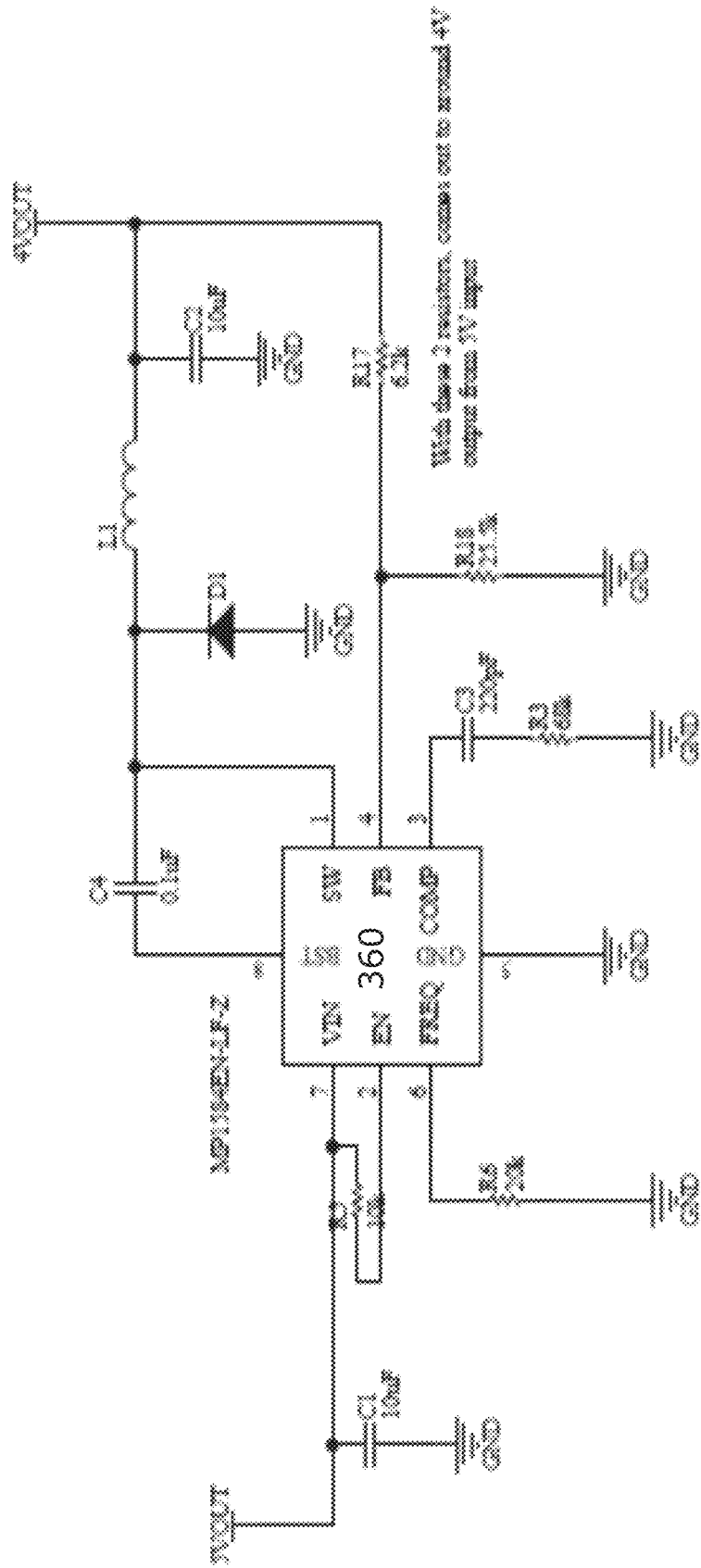
FIG. 3D is a schematic diagram of an electrical step-down converter of the biometric sensor device in FIG. 2A, according to an aspect of the disclosure.

FIG. 3D is another schematic diagram 307 of a step-down converter of the biometric sensor device. The step-down converter includes MP1584EN-LF-Z circuit 360 and supporting electronic devices. The step-down converter steps down the voltage in the base unit to support operation of electronic devices that require lower operating voltages.

As described above, the biometric data (e.g., video, speech, accelerometer, gyroscopy, pupillometry, ECG, etc.) collected by the biometric sensor device is time synchronized across sensors within and across each person (e.g., all participants) involved in the session (social or otherwise). When involving two or more participants, this provides data analyses (e.g., for ASD research and clinical characterization such as a diagnosis or assessment of therapeutic efficacy across time), for example, to focus on ways social communication signals and repetitive behaviors are transmitted and responded to between participants, and ways in which repetitive behaviors and arousal/anxiety affect coordinated social communication.

For ease of use, each camera sensor of the biometric sensor device is rotatable, accommodating recording needs at various angles, such as when a clinician performs specific psychological assessments at 90 degrees from a child. Full rotation of the cameras is also possible to record the same participant(s) in a stereoscopic camera set, turning 2D cameras into 3D depth cameras. This may be important for gross motor behavior tracking of participants. The addition of depth provides an additional signal for separating tracking of an individual's movements from that of background noise as well as from the bodies of other individuals present. Use of the cameras for whole body (including face and head) tracking provides accurate measurements of motor movement in instances where use of wearables may not be possible and when wearables do not provide as much information about the movements. Full or partial body tracking using these cameras can also easily enable tracking of potentially dozens of subjects simultaneously, forgoing the need to attach multiple wearable sensors to multiple subjects. The ability to easily measure multiple subjects simultaneously is beneficial to implementation of the biometric sensor device in everyday social or other contexts.

In this example, each sensor has been developed and optimized to be as small as practically possible to minimize their impact on natural behaviors of the participants. In one example, each wireless device (e.g., accelerometer/gyroscope wearable and ECG probe) are approximately the diameter of a 25 cent coin or a watch face, and light enough to be adhered to any part of the body without confounding movement.

Together, the biometric data acquired with these synchronized technologies enables the development of improved statistical models of social behavior, repetitive behavior, solitary behavior, and communicative behaviors through granular analysis of speech, language, vocal acoustics, heart rate variability, pupillary responses, limb/body motor signatures, facial motion (e.g., gestures, expressions), eye gaze behavior, and the like for each person, and as a complex synchronized set of signals within and between individuals.

It is noted that time synchronization occurs between different sensor data for the same participant and between participants. For example, multiple sensor signals for participant P1 are all time synchronized together for participant P1, and multiple sensor signals for participant P2 are all time synchronized together for participant P2. In addition, the sensor signals of participant P1 are time synchronized with the sensor signals of participant P2. This time synchronization allows for comparison between the signals.

The compactness of the biometric sensor device enables it to sit on a tabletop, stand (see FIG. 1A), positioned on the floor between individuals, or suspended from the ceiling, minimizing interference when recording the session. In one example, the cameras are mounted on an adjustable arm 204, allowing height adjustments. In another example (not shown), the camera's arm is replaced with a shorter arm which may or may not be adjustable to produce a biometric sensor device having a more compact configuration that may be preferable in some situations. In another example, an extension pole (see FIG. 1B) supports the biometric sensor device for floor mounting. For example, an extension pole on a tripod attaches to the biometric sensor device base, and positions the biometric sensor device at various heights relative to the participant(s).

For ease of use, the wireless devices (e.g., accelerometry/gyroscopy and ECG devices) can be preregistered to the biometric sensor device. At startup, CPU 330 automatically synchronizes all wireless devices in the proximity of the biometric sensor device to the high-resolution cameras and to each other. The external antenna sits between the cameras and ensures delivery of high-resolution data from up to dozens of wireless devices simultaneously from various distances.

For example, the wireless ECG wearable may attach to the upper abdomen via two adhesive electrodes to which the ECG sensor fastens on. The operator may attach wearable accelerometry/gyroscopic device(s) to the wrist(s) and/or ankle(s) of the participant(s) via a soft sweatband or a watchstrap. The devices are light and small enough that they can also be attached to any part of the body using adhesive (e.g., medical tape).

In this example, the biometric sensor device requires minimal setup, and is managed by a toggle switch on the side of the unit facing the operator. An array of switches on this side of the unit allow for customizing the recording session to any combination of sensor modalities (e.g., video, limb wearables, ECG). A display (e.g., OLED display) located on the side of the unit helps keep the operator informed about the recording time (and battery life for wireless devices) and alerts the operator when the batteries need to be changed or charged.

When not using the camera or its microphones, the operator may place the biometric sensor device in a location out of the way, while continuing the synchronized recording of wireless limb, head, and torso wearables and ECG data.

During operation, the computer may write data to removable memory cards (e.g., micro-SD cards) for later analysis. This improves flexibility of use, allowing the operator to exchange memory cards for more storage space as the biometric sensor device needs it. The computer (e.g., using a USB 3 high-speed micro-SD hub connected to a local computer running the software, or using the wireless transceiver communicating with a remote computer running the software) may automatize memory card data upload.

Throughout the description, a specific example of classifying and scoring participants into a neurological classification/scoring is used to describe the operation of the biometric sensor device and the classification/scoring algorithm. However, it is noted that the biometric sensor device and the algorithm may use the information captured during the session to classify one or more participants into various classifications/scorings including but not limited to psychological classifications/scorings (e.g., depression, anxiety, romantic compatibility, job compatibility, etc.), neurological classifications/scorings (e.g., ASD, dementia, progressive motor neuron disease, etc.), and the like. The biometric sensor device may also be used to measure change in behaviors across time that might represent deterioration or amelioration of the quantitative phenotypes across time (e.g., due to treatment side effects, natural history of the phenomenon, or positive treatment effects).

It is also noted that the description describes a specific example of a dyadic interaction between two participants captured and analyzed by the biometric sensor device. However, the biometric sensor device could capture and analyze sessions between more than two participants. For example, the device could capture sessions between multiple participants in a group interaction. In another example, the device can be used to capture the behavior of just one person engaged in a solitary activity, or a group of individuals each engaged in solitary activities, or a group of individuals where some are interacting with others and others are engaged in solitary activities. Comprehensive digital quantitative phenotypic measurement is feasible in every combination with this device.

Training/Prediction Process Overview

Figure 4A:
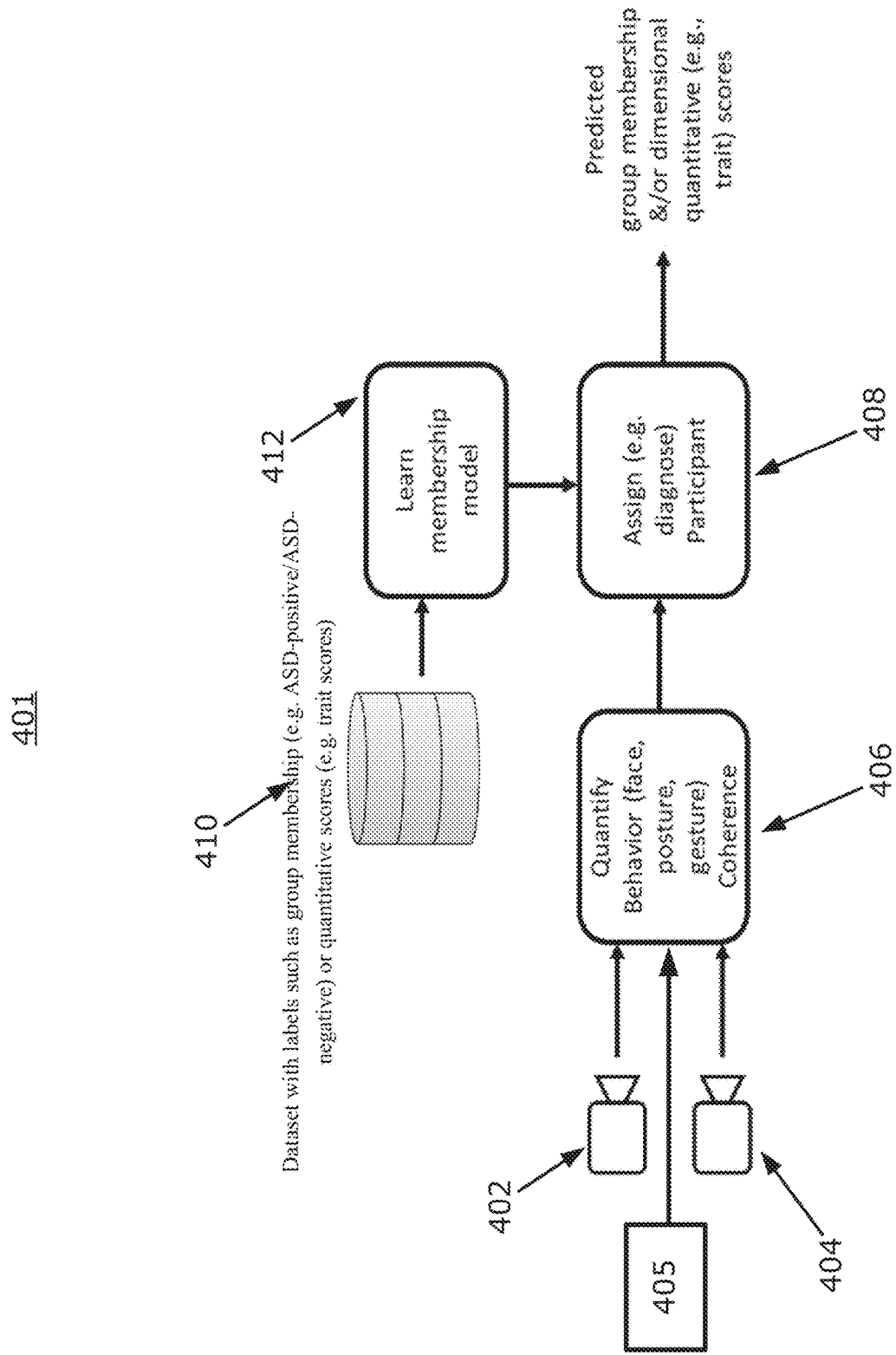
FIG. 4A is a flowchart of a digital quantitative phenotyping process, according to an aspect of the disclosure.

FIG. 4A is a flowchart 401 of a digital quantitative phenotyping process performed by the biometric sensor device for classifying/scoring a participant (e.g., classify the participant as ASD positive/negative, and score the participant as ASD mild/moderate/severe). For example, when classifying/scoring for a medical condition, this digital quantitative phenotyping process is beneficial for diagnosing patients, scoring severity of the diagnosed condition, assessing patient treatment/progress, and the like.

One study by the inventors, for example, found that analyses of a 3 minute unstructured dyadic conversation could predict the correct diagnosis of study participants as having autism or not with 89% accuracy from video input of facial movements alone (e.g., not using speech, body part sensors, video of body movements, pupil movements, or limb gesture data that is also collected by this device). This was significantly more accurate than a group of autism clinical experts who tried to predict diagnosis by watching the same 3 minute dyadic conversations. Because it takes an experienced doctor/clinician at least 30 minutes and often times several hours to establish an accurate diagnosis of autism, the biometric sensor device can be used to greatly shorten evaluation times. Moreover, each person with autism also received a severity score that comported well with other standardized autism severity indices. Thus, data analyses allowed prediction of group membership and prediction of individual group members along a single severity dimension. However, multidimensional prediction is also feasible. Being able to score each participant on a severity dimension and sub-dimensions has beneficial uses for monitoring treatment efficacy across time, as well as for monitoring deteriorations in the person's condition due to the natural history of the condition(s) and/or to unwanted side effects from certain therapeutic interventions (e.g., motor tics that often accompany psychotropic medications). The biometric sensor device can be used in various locations including in a clinic and away from the clinic (e.g., in the person's home and other settings such as schools and community organizations) to quickly provide a status update and guide treatment decisions and care management. The biometric sensor device can repeat measurements as often as needed.

Another study by the inventors, for example, found that analyses of a 3 minute dyadic conversation predicted the correct diagnosis of study participants as having autism or not with 91% accuracy using video input of facial movements in combination with lexical features from the conversation. These included the types of words spoken, specific pronouns (e.g. I or we), concrete nouns, and words referring to psychological processes (e.g., "think" and "feel"). In another study the use of lexical features alone predicted the correct diagnosis of study participants as having autism or not with 84% accuracy from a 3 minute dyadic conversation. Yet another study used acoustic properties of the voice to predict the diagnosis.

There are two basic processes in flowchart 401 (e.g., algorithm training and measurement/prediction). The processes (e.g., training and measurement/prediction) described throughout are performed by a computer. The "computer" that performs the measurement/prediction may be the processor within the biometric sensor device, or a computer external to the biometric sensor device such as a personal computer or cloud computers. The "computer" may also be a combination of both the biometric sensor device computer and an external computer(s).

The first process is a training process as illustrated by steps 410 and 412. Step 410 stores training datasets of previously recorded sessions, where participants (e.g., ASD subjects) have already been accurately classified/ranked/scored for ASD (e.g., by experienced autism clinicians after extensive diagnostic workups). In step 412, a computer (e.g., the biometric sensor device or an external computer including cloud computer) trains the ASD prediction model using these training datasets. Details of this training process is described with references to later figures.

The second process is a measurement/prediction process as illustrated by steps 402, 404, 406 and 408. Steps 402 and 404 use the cameras/microphones and wearable sensors 405 of the biometric sensor device to capture data during the session between the participants (e.g., evaluated subject and an interlocutor). If only one participant is being evaluated, step 404 is not needed, and rather than an interaction, step 404 and 405 captures solitary activity of the participant. In steps 406 and 408, the computer quantifies behavior (e.g., facial gestures, speech, etc.) and physical characteristics/signals of the participant(s) and then predicts the classification and quantitative phenotypic scores of the evaluated subject based on this quantified sensor data. Details of this measurement/prediction process are also described with references to later figures.

Figure 4B:
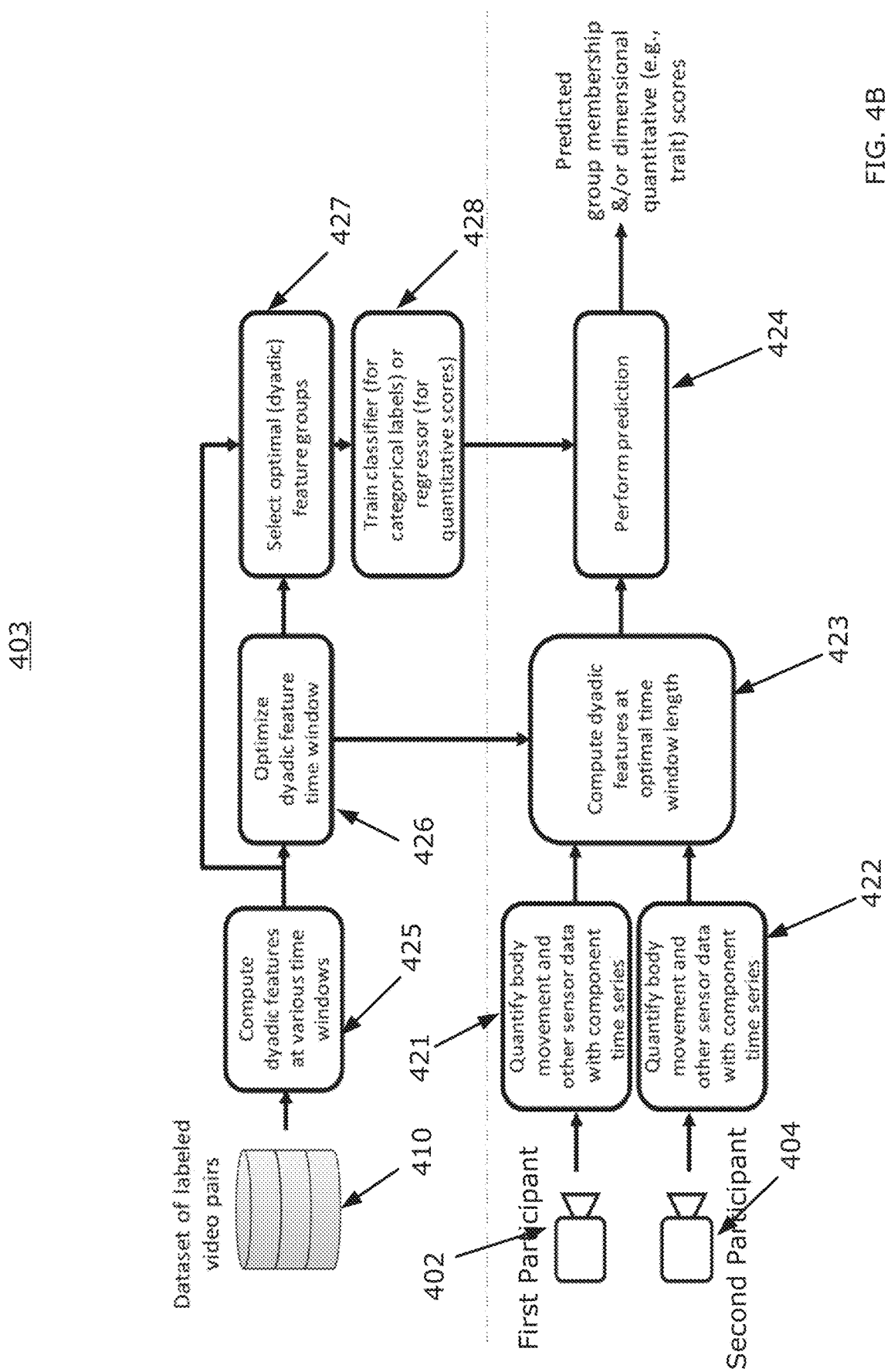
FIG. 4B is a more detailed flowchart of the digital quantitative phenotyping process in FIG. 4A, according to an aspect of the disclosure.

FIG. 4B is another flowchart 403 showing more details of the training process and measurement/prediction process in FIG. 4A. Details of the training process are shown above the dashed line, while details of the measurement/prediction process are shown below the dashed line.

In step 425 of the training process, the computer computes features of the dyadic interactions of the training datasets stored in database 410. In step 426 of the training process, the computer optimizes the dyadic feature time window (e.g., the window for observing the dyadic features). In step 427 of the training process, the computer selects optimal dyadic feature groups (e.g., groups of corresponding facial features and other detectable features that are optimal for classifying the participants in the training dataset or for predicting clinical severity scores). In step 428 of the training process, the computer trains the predictor (e.g., a classifier or regressor depending on whether the prediction involves classification or scoring) based on the selected optimal feature groups. The selection of feature groups is fully automatic and not specific to a certain application, which ensures that the prediction algorithm can be applied to a variety of applications such as classifying/scoring the subject for the psychiatric or neurological disorder(s) (e.g., dementia and other neurocognitive disorders) or for predicting romantic compatibility, or change in psychological closeness due to treatment (e.g., marital counseling) or for predicting job success as part of a job interview where good social communication skills are relevant. The process can be easily adapted for singular participants (e.g., not dyadic) or group interactions.

After the training process trains the prediction algorithm, the computer can perform classification/scoring of new subjects in the measurement/prediction process. For example, in step 422 of the measurement/prediction process, the computer quantifies the behaviors and dynamic physical characteristics/signals of participant(s) (e.g., evaluated subject and an interlocutor) recorded during a new session. As described above, these physical characteristics may include but are not limited to body movement, facial gestures, speech, heart rate, blood pressure, electrophysiological signal and the like. In step 423 of the measurement/prediction process, the computer computes the features at the optimal time window length determined during the training process. Then in step 424 of the measurement/prediction process, the computer performs the prediction by using the trained predictor to classify/rank/score the subject within their classification category with respect to how close they are to the boundary of the group (e.g., severity and other dimensional attributes).

Figure 4C:
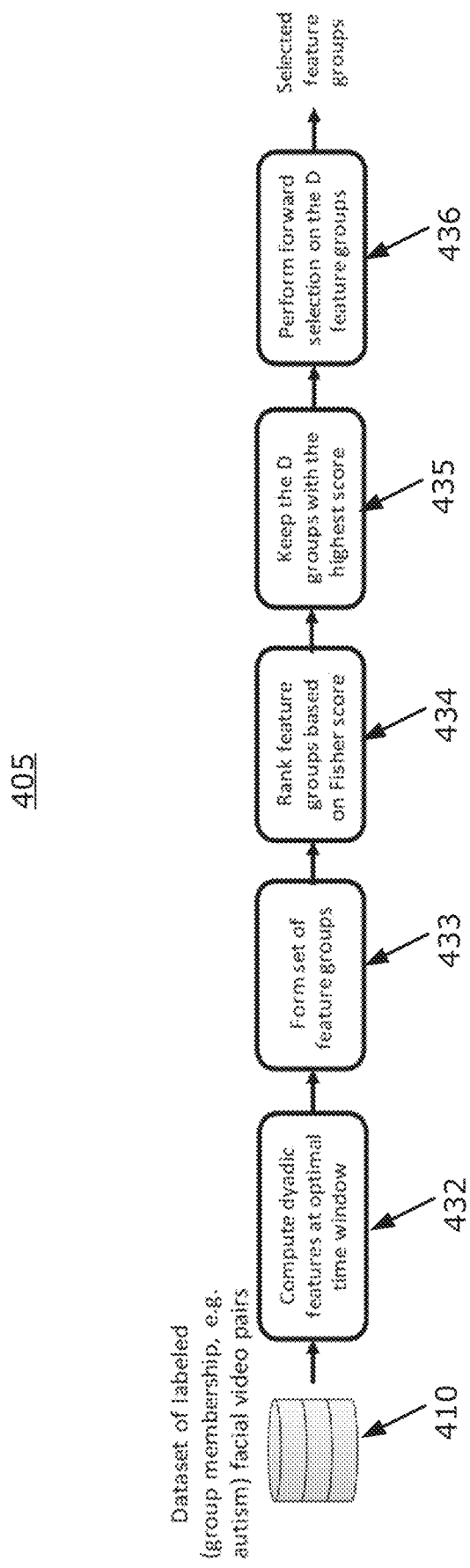
FIG. 4C is a more detailed flowchart of the group selection process in FIG. 4B, according to an aspect of the disclosure.

As mentioned above, the computer performs feature group selection during the training process. FIG. 4C is a flowchart 405 of the details of the feature group selection process. In step 432, the computer computes the features of the data in dataset 410 at the optimal window. In step 433, the computer forms the feature groups, and then ranks the feature groups in step 434. The feature groups with the highest ranking of accuracy are maintained in step 435, and then in step 436, the computer performs selection on the maintained groups (e.g., selects a group of facial features that best predict ASD).

FIGS. 4A-4C describe the training process and measurement/prediction process. Further details of these two processes for classifying/scoring participants for neurological disorders (e.g., ASD) are now described with respect to the remaining figures.

ASD Training/Prediction

Figure 5A:
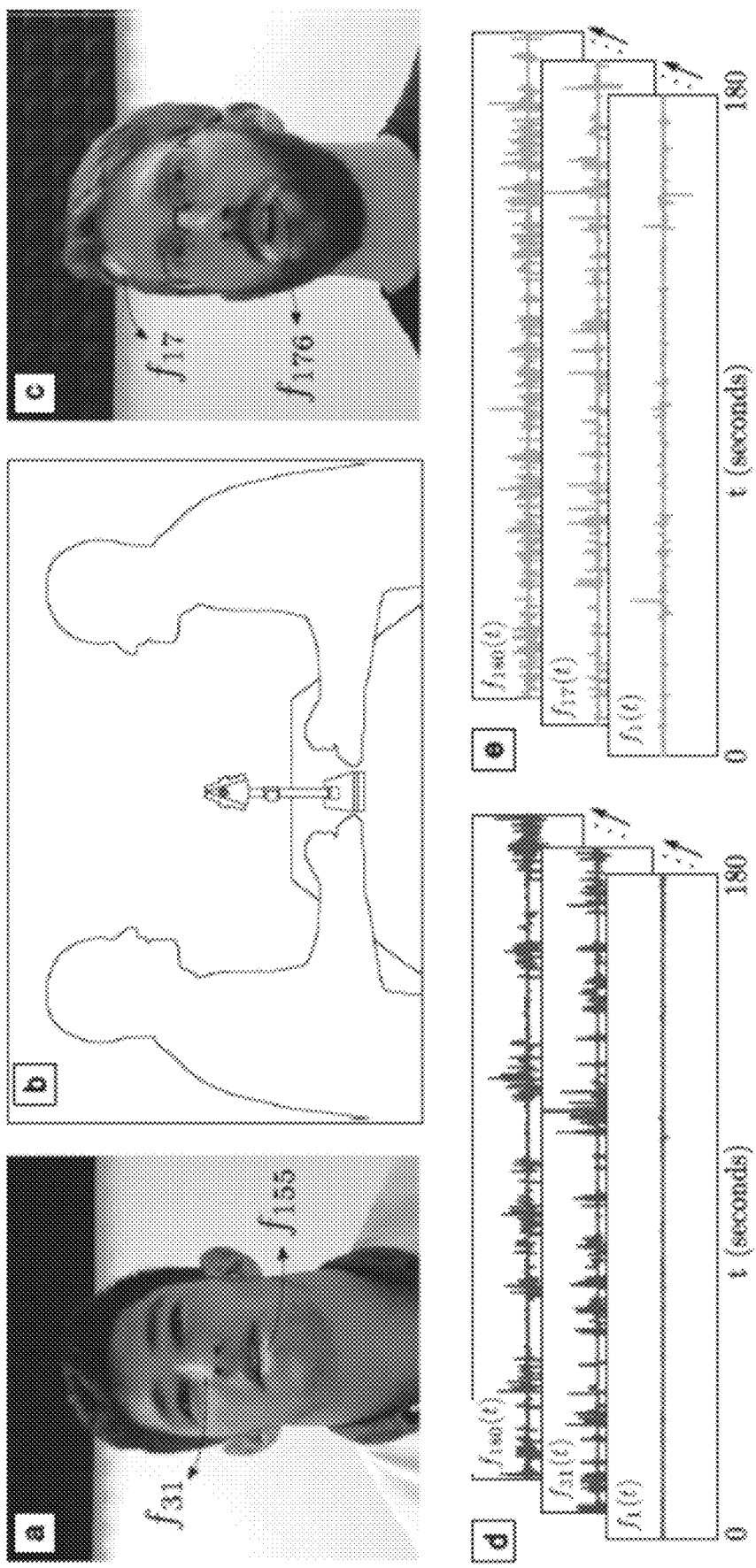
FIG. 5A is a view of a dyadic interaction between two participants which shows time series outputs for detected facial movements, according to an aspect of the disclosure.

FIG. 5A shows an example dyadic interaction between an interlocutor (e.g., ASD negative participant) and a young adult (e.g., an individual being evaluated for ASD). However, the illustrated procedure is not limited in its implementation to young adults. For example, other data provide comparable efficacy examples for children under age 18 years using the same procedures. The biometric sensor device is compatible with assessment goals for any aged person or group of people. An example of time series outputs from steps 421 and 422 in FIG. 4B that quantify facial movements from a conversation over a time period T are shown in FIG. 5A. Although facial movements are detected and analyzed in this example, it is noted that audio signals (e.g., language and acoustic properties of speech such as rate of speech, pronunciation, prosody, words, spaces between words, frequency of words, frequency of voice, etc.), other movements (e.g., limb, torso, pupils, etc.), and physiological signals (e.g., ECG signals) are also recorded and synchronized within and between participants with the biometric sensor device (e.g., by microphones and wearable sensors) and analyzed by the algorithm described below to classify/score the subject. These various signals could be used independently or in conjunction with one another in the analysis.

For example, window (a) shows the interlocutor (e.g., participant that does not have ASD in this example) in the conversation, while window (c) shows the participant (individual being evaluated for ASD) in the conversation. Window (b) shows the recording setup with the interlocutor and the participant facing each other, and the biometric sensor device placed in between with a full-frontal perspective view of each for synchronized video recording.

Many techniques may be used to quantify facial movements. This may include the Facial Bases method, the OpenFace method, or the like that use image analysis techniques to identify and track facial features of a participant(s). In the example described below, the computer quantifies the facial movements in each video using the Facial Bases technique. This technique encodes the facial behavior in a video through 180 time sequences, $f_1(t)$, $f_2(t), \ldots, f_{180}(t)$, where each sequence provides information about a movement that occurs in a particular region of the face or the head. Each sequence $f_j(t)$ is a monadic feature. The monadic features are computed both from the participant 421 (see window (e)) and the interlocutor 422 (see window (d)). Other comparable techniques (besides the Facial Bases Technique) are also supported by the device and the data analytic framework. In this example, the Facial Bases technique used to compute the features $f_j(t)$ requires the left eye, right eye, and the mouth regions to be cropped in the captured video separately at each frame. For this purpose, the computer can use a facial landmark detection tool to crop the regions, and then put the cropped frames together to form three 3-minute videos for the three regions. The number of regions can be increased or decreased which can improve results. Similarly, the length of the video can vary. Frames where facial landmark detection failed are dropped from the analysis. The computation of the features $f_j(t)$ benefits from image stabilization across frames as cropped sequences have visible jitter due to imprecise landmark localization at each frame. Therefore, the computer can also eliminate jittering in each region's sequence through a video stabilization technique. To counter possible accumulated drift error over time, stabilization is performed independently for sequential sets of 100 non-overlapping frames across the entire video, resulting in 54 segments of each facial region for a 3-minute video sequence recorded at 30 frames per second (fps). Next, features $f_j(t)$ based on Facial Bases are computed independently from each of the 100-frame segments. Each of the 100-frame segments yields a time series $f_j(t)$ of 99 points, as the approach derives information from successive frames from a differential equation. All 54 time series are merged into a time series $f_j(t)$ of 5346 points. This process is repeated for 180 features $f_1(t)$, $f_2(t), \ldots, f_{180}(t)$, resulting in 180 time series of 5346 points, less dropped frames per conversation. Other numbers of features are also viable for the analysis.

To distinguish between the monadic features of the interlocutor and the participant, the notations $f_j^i(t)$ and $f_j^p(t)$, are used respectively. Some features are semantically interpretable. For example, $f_{176}^p(t)$ is activated when the lip corner of the participant moves upwards/downwards (see FIG. 5A window (c)), and $f_{155}(t)$ is activated when the subject's lower lip moves, which typically occurs when the subject is talking (see FIG. 5A window (a)). Some features are activated exclusively with non-planar head rotations, as they are located in regions that cannot be moved with facial expressions. For example, $f_{31}(t)$ is located on the side of the nose (see FIG. 5A window (a)) and $f_{17}(t)$ is located on the side of the forehead (see FIG. 5A window (c)).

Figure 5B:
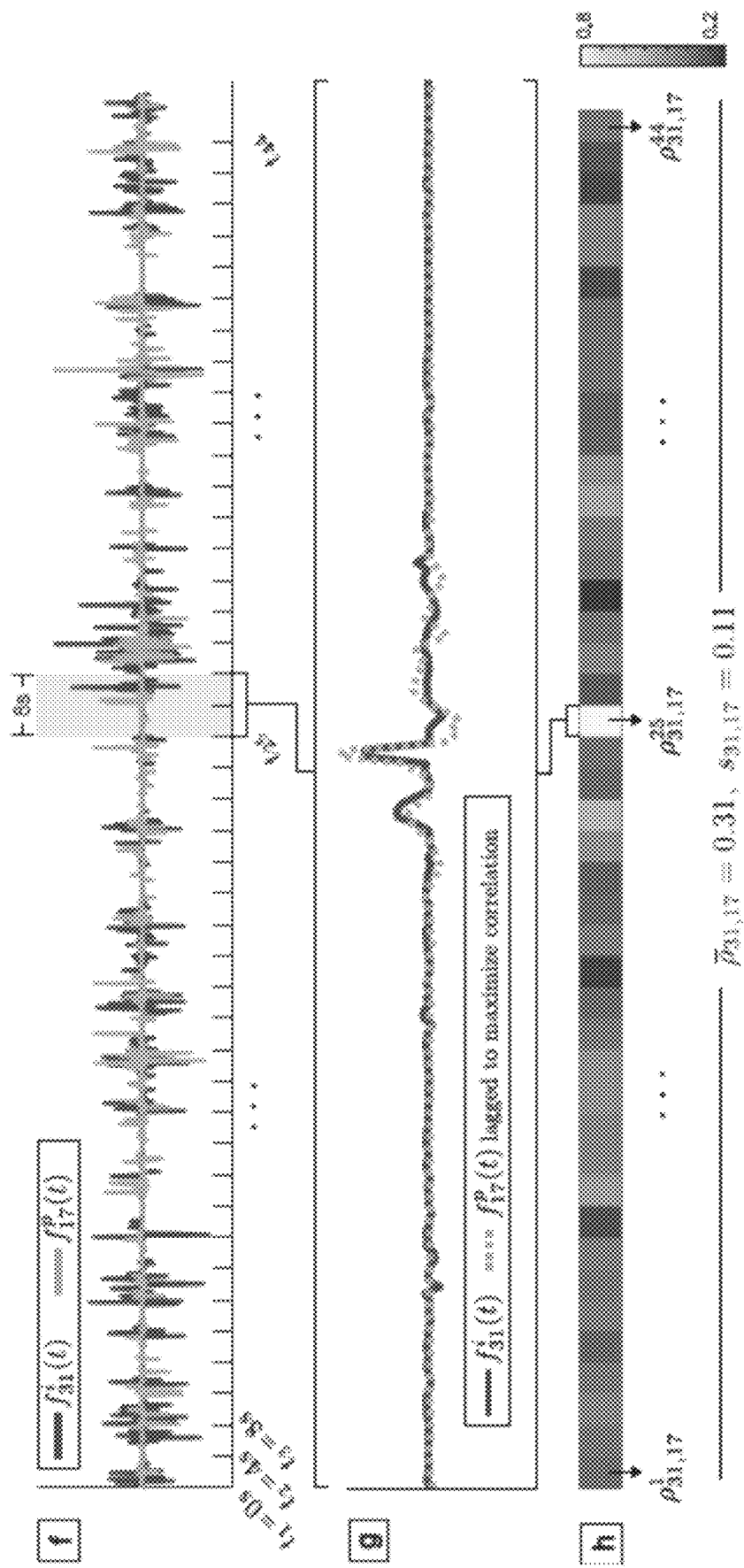
FIG. 5B is a view of the overlay and correlation between the time series outputs in FIG. 5A, according to an aspect of the disclosure.

Next, the computer encodes the dyadic interaction between the interlocutor and the participant via, for example, windowed or standard cross-correlation (e.g., time-lagged correlation across varying lag values) between all possible monadic feature pairings of the interlocutor and the participant, $(f_1^i, f_1^p), (f_1^i, f_2^p), \ldots, (f_2^i, f_1^p), \ldots (f_{180}^i, f_{180}^p)$. Specifically, the computer computes the cross-correlations from multiple local time windows (e.g., windowed cross-correlation) for each pairing to compare the features. FIG. 5B illustrates the computation of windowed cross-correlation (for time window length of 8 seconds) for one such pairing, namely $(f_{17}^i, f_{31}^p)$.

The time window length in windowed cross-correlation is an important parameter, and different window lengths may be optimal for different applications (e.g., the optimal time window for dyadic conversations with children is typically longer than that for the dyadic conversations between adults).

The computer uses a data-driven analysis to determine the optimal time window length in step 426. In one implementation, the computer uses leave-one-out cross-validation (LOOCV) to evaluate prediction performance on an example data set of 44 samples of dyadic conversations with different study participants. The number of samples and procedure of evaluation may vary. For example, let T be an arbitrary time window length. To determine the optimal time window at each of the 44 LOOCV folds, the computer uses 43 samples for the training, and constructs a data matrix $X_T$ where each row contains all the dyadic features that are computed from one sample by setting the time window to a value of T. In this particular implementation, the computer may compress the matrix $X_T$ via a compression algorithm (e.g., principal component analysis (PCA)) and obtain a matrix $Z_T$. The application of PCA aims to reduce the possibility that the highly correlated values in $X_T$ yield a suboptimal time window. With larger data sets, a different approach may be taken where dimensionality reduction is not a prime concern. Each row of the PCA-transformed data matrix, $Z_T$, represents one of the 43 samples. The computer constructs two sets $Z_T^+$ and $Z_T^-$. The set $Z_T^+$ contains all the rows of $Z_T$ that correspond to ASD-positive samples, and $Z_T^-$ contains the rows of $Z_T$ that correspond to ASD-negative samples. The computer computes two average vectors: $z_T^+$, the average of all the vectors in $Z_T^+$, and $z_T^-$, the average of all the vectors in $Z_T^-$.

The goal is finding the optimal time window length T* that maximizes the Euclidean distance between the class means:

$$T^* = \arg_{T \in \mathcal{T}} \max \|z_T^+ - z_T^-\| \qquad (1)$$

Distance metrics other than the Euclidean distance can also be used. The computer performs the search towards maximization over time window lengths of 2, 4, . . . , 64, that is, $\mathcal{T}=\{2^k\}_{k=1}^6$. The optimal length, T*, in the example dataset with 44 adult samples is 8 seconds in all of the 44 folds of LOOCV. Once the optimal time window length for windowed cross-correlation is determined, the dyadic features are computed (step 423) via windowed cross-correlation between the features of the participant and the features of the interlocutor. FIG. 5B shows this process for the features $f_{17}^P(t)$ and $f_{31}^i(t)$. In this example, cross-correlation is computed first for the 8-second time window that starts at $t_1=0s$, and then next for the window that starts at $t_2=4s$. The process continues until the computer arrives at the last 8-second time window of the 3-minute videos (e.g., $t_{44}=172s$). Window (g) shows the time window that starts at $t_{25}=96s$, and shows $f_{17}^P(t)$ after shifting it (see dotted curve) based on the lag value yields the maximum of the cross-correlation. The maximum of the cross-correlation is denoted with $\rho_{31,17}^k$ where k indicates the time window. The minimum and maximum allowed lag values in cross-correlation in this example are −4 and 4 seconds. The computer summarizes the maximal cross-correlations computed from all the 44 time windows throughout the 3-minute videos (e.g. $\rho_{31,17}^1$, $\rho_{31,17}^2$, . . . $\rho_{31,17}^{44}$) by computing their average, $\bar{\rho}_{17,31}$, and their standard deviation, $s_{17,31}$, as shown in window (h). For the time window that starts at $t_{25}$, the maximum of the cross-correlation is the correlation between the dotted and solid curves in window (g).

Since the computer extracts two dyadic features per pair (average and standard deviation) and processes all possible pairings of monadic features of the interlocutor and the participant $(f_1^i, f_1^P), (f_1^i, f_2^P), \ldots, (f_2^i, f_1^P), \ldots (f_{180}^i, f_{180}^P)$, the total number dyadic features is 2×180×180=64,800. The computation of those 64,800 features corresponds to step 423. The computer groups those features along the participant, such that for each of the 180 monadic features of the participant $f_i^P(t)$, the computer creates a 360-dimensional vector $\rho_i$ that contains all the dyadic features:

$$\rho_i = [\bar{\rho}_{1,i}, s_{1,i}, \bar{\rho}_{2,i}, s_{2,i} \ldots \bar{\rho}_{180,i}, s_{180,i}]. \quad (2)$$

Each $\rho_i$ is referred to as a feature group, where a 3-minute conversation between the participant and the interlocutor with the 180 feature groups is represented as $\{\rho_1, \rho_2, \ldots, \rho_{180}\}$.

During prediction, the computer may use a subset of those feature groups that are selected automatically. Feature group selection improves performance and is beneficial for interpreting the predictor. The selected feature groups provide information about which behaviors of the participant are used by the predictor for classifying/scoring the evaluated subject(s). Note that it is also possible to not group the features, and instead perform selection over the individual 64,800 dyadic features. However, the number of dyadic features is much larger than the size of the dataset (e.g., 44), and the feature sets selected in such cases may be unstable. That is, the features selected in different subsamples of the dataset are different, which deteriorates performance and compromises the semantic interpretability of the selected features. Grouping the features is a good approach to overcoming instability. Standard (e.g., individual) feature selection can also be performed if the number of samples in the dataset is large enough to prevent instability during selection.

For the prediction performed in step 424, the computer may use linear support vector machines (SVMs) in conjunction with feature group selection, and report results with fully automatic (nested) LOOCV, so as to be able to treat the prediction accuracy results as generalizable to new samples drawn from the parent population with similar clinical attributes. Predictors other than linear SVMs can also be used (e.g. deep learning algorithms). The computer sets the parameters of the classifier and selects the feature groups independently at each fold via inner cross-validation and uses the classifier thus built on the one test sample that is left out.

In the example, feature group selection is performed prior to prediction not only to improve classification/scoring accuracy, but also to be able to interpret the predictor. Prior to starting the selection process, the computer may compress each feature group separately by applying PCA. Group selection is essentially a forward selection approach. Specifically, the computer starts with an empty set and expands it iteratively until adding more feature groups does not improve performance in the inner cross-validation fold. In order to improve computational efficiency and/or performance, the computer can reduce the number of candidate feature groups prior to forward feature group selection as shown in steps 434 and 435.

Feature group selection requires selecting a subset from the set of 180 feature groups, $\{\rho_1, P2, \ldots, \rho_{180}\}$, that maximizes performance. As described above, a feature group $\rho_i$ is defined in equation 2.

Since the computer uses LOOCV for performance evaluation, the computer selects feature groups separately at each cross validation fold. That is, at each fold, the computer aims to find a subset that contains D* feature groups. With 44 samples in total, the computer uses 43 samples to select the feature groups that will be used on the one sample left out according to LOOCV. Let $\mathcal{F}^*$ be the set that contains the indices of the feature groups selected at a particular fold, $\mathcal{F}^* = \{f_1^*, f_2^*, \ldots, f_{D^*}^*\}$, and $\mathcal{P}^*$ contain the corresponding feature groups (e.g., $\mathcal{P} = \{\rho_{f_1^*}, \rho_{f_2^*}, \ldots, \rho_{f^*_{D^*}}\}$).

As described above, the computer follows a forward selection approach: 1) start with an empty set, and 2) iteratively add feature groups until no improvement in classification/scoring accuracy (e.g., over the inner fold—the 43 samples) is observed. Since the computer uses classification/scoring accuracy as a criterion of selection, this approach is categorized as a wrapper approach. As described below, the computation of classification/scoring accuracy is of $\mathcal{O}(D^2)$ computational complexity where the candidate feature groups at each iteration of forward feature selection is D.

As described above, to reduce computational complexity, the computer reduces the number of candidate feature groups prior to forward feature group selection through a filter approach. It is possible to represent the feature group using one feature from the group or the mean of all features within the group. However, such approaches may lead to the loss of important information. Thus, the computer may choose to represent each group in a multi-variate manner after compressing it through PCA.

Figure 6A:
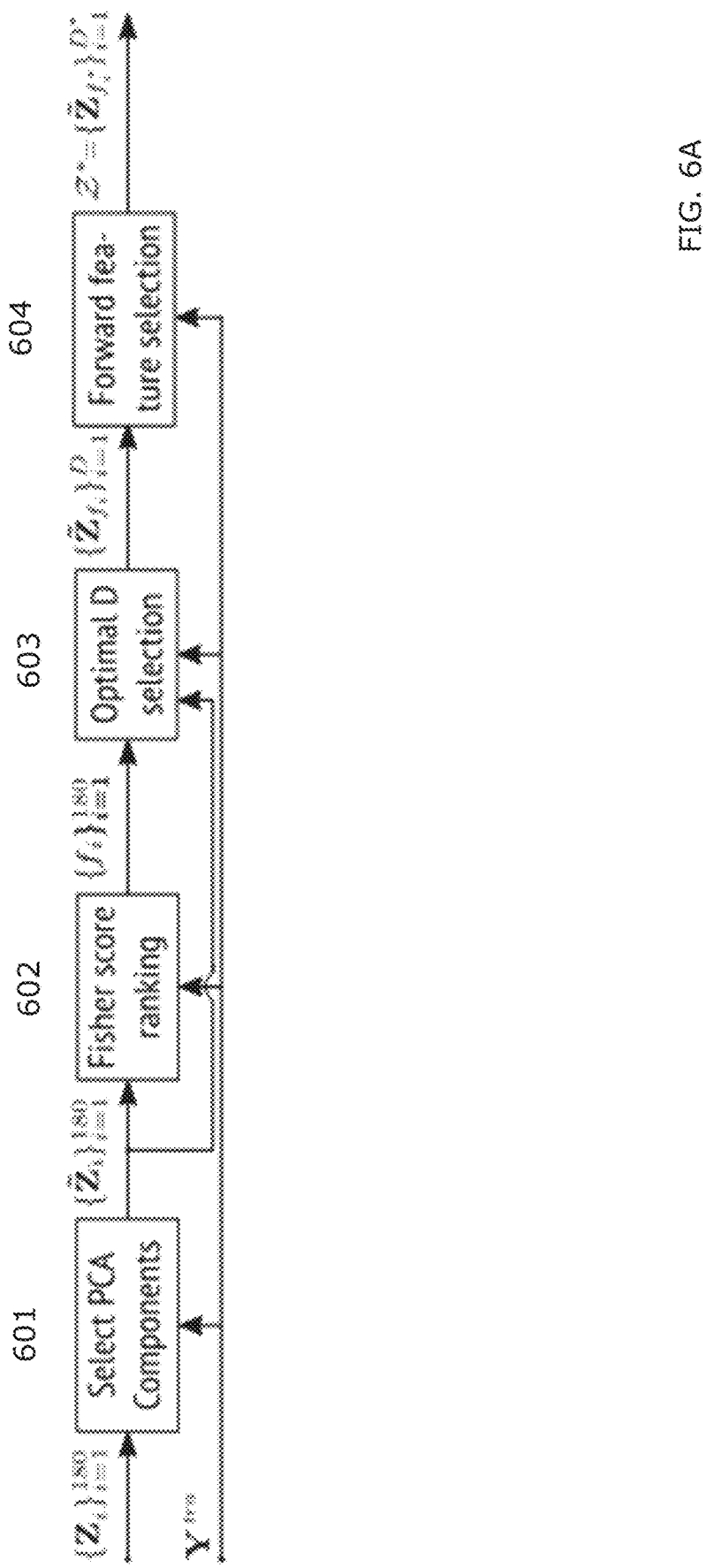
FIG. 6A is a flowchart of a feature group selection pipeline, according to an aspect of the disclosure.
Figure 6B:
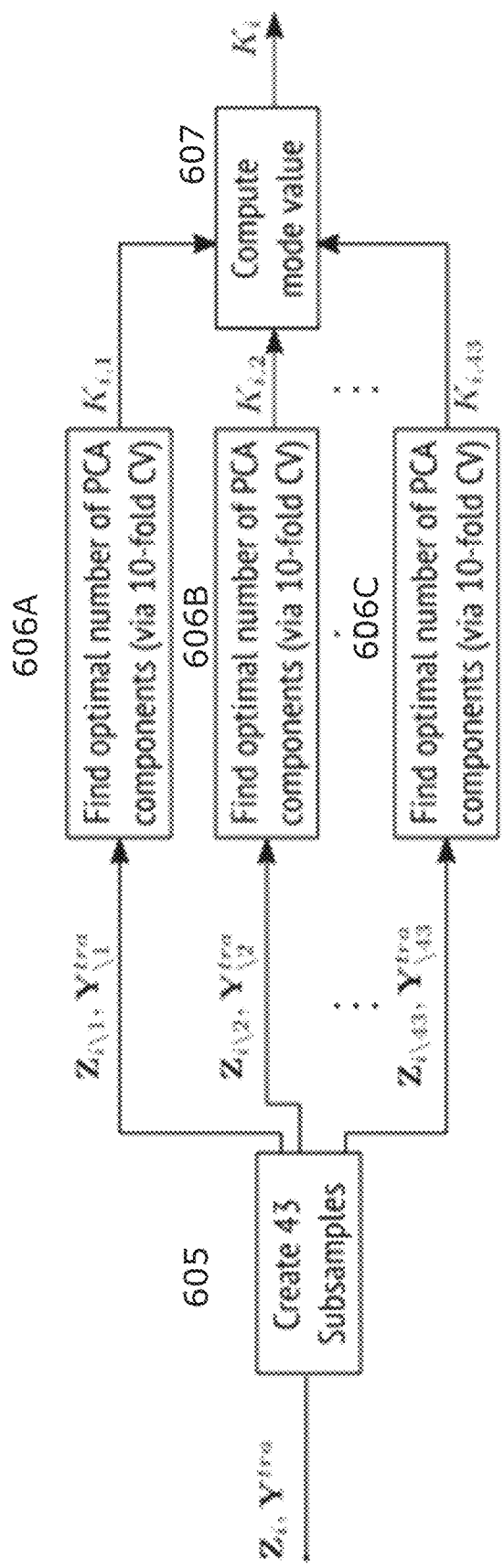
FIG. 6B is a flowchart of a first step of the feature group selection pipeline in FIG. 6A, according to an aspect of the disclosure.

The group selection process described above is further detailed in FIGS. 6A-6C and below. FIG. 6A outlines the overall pipeline for one LOOCV fold. The $Y^{tra}$ in FIG. 6A represents the labels of the 43 training samples of the fold.

The input to the pipeline of FIG. 6A is the set of all 180 feature groups (transformed by PCA), and the output is the subset of selected feature groups. The PCA-transformed feature groups that are used for the pipeline in FIG. 6A (e.g., $\{Z_1, Z_2, \ldots, Z_{180}\}$) can be obtained as follows. Let N be the number of all the samples (e.g., N=44 in our case), $\rho_i^n$ be the ith feature group of the nth sample obtained as in Eq.

(2), and $X_i$ be the data matrix for the ith feature (e.g., the N×360-sized matrix whose rows are $p_i^n$). By applying PCA to $X_i$, the computer obtains a matrix $Z_i$. The nth row of this matrix, $z_i^n$ represents the PCA coefficients corresponding to the sample $p_i^n$. Then, the computer removes from the matrix $Z_i$, the row that corresponds to the test sample of the LOOCV process. As a result, the matrix $Z_i$ contains 43 rows. The computer applies this process to all the feature groups (e.g., i=1,2, . . . , 180) and thus obtains 180 PCA-transformed matrices, $\{Z_1, Z_2, \ldots, Z_{180}\}$.

Step 601 of FIG. 6A (shown in detail in FIG. 6B) represents the dimensionality reduction process that takes places on the PCA-transformed data. To reduce the dimensionality of the ith feature group, the computer selects the first $K_i$ components of the PCA-transformed data. That is, the first $K_i$ columns of the matrix $Z_i$ are selected. The computer denotes the matrix thus compressed with $\tilde{Z}_i$. The computer sets $K_i$ via inner cross-validation on the 43 samples. Specifically, the computer subsamples (step 605) the data matrix 43 times by leaving out one sample each time, and obtains 43 candidate values, $\mathcal{K} = \{K_{i,1}, K_{i,2}, \ldots, K_{i,43}\}$. The computer sets $K_i$ as the most frequent value (e.g., mode) in the set $\mathcal{K}$ (step 607). Each of the candidate values, $K_{i,n}$, is obtained with 10-fold stratified cross validation (steps 606A-606C) on the training data (e.g., on the 42 samples) of the corresponding inner LOOCV fold.

Steps 602 and 603 in FIG. 6A represent the filter approach to reduce the set of candidate features from 180 to D features. In step 602, the computer ranks the 180 feature groups based on their Fisher score and then in step 603 (detailed in FIG. 6C) the computer selects the first D of the ranked features. The output comprises the rankings $f_1, \ldots, f_{180}$. The relationship $f_i > f_j$ implies that the ith feature group has a larger Fisher score than the jth group (e.g., scores other than Fisher can also be used for ranking given that they are applicable to multi-dimensional features as well as single-dimensional features). While computing the Fisher score of the ith feature, the computer uses only the first two columns of $\tilde{Z}_i$ (rather than all the columns) due to two reasons: (i) the number of columns is different for each feature group, which impacts the score (e.g., groups with higher number of columns have higher Fisher score), and (ii) the scores become more similar (they approach to their maximum, 1) and lose discrimination power as they are computed from more columns.

Figure 6C:
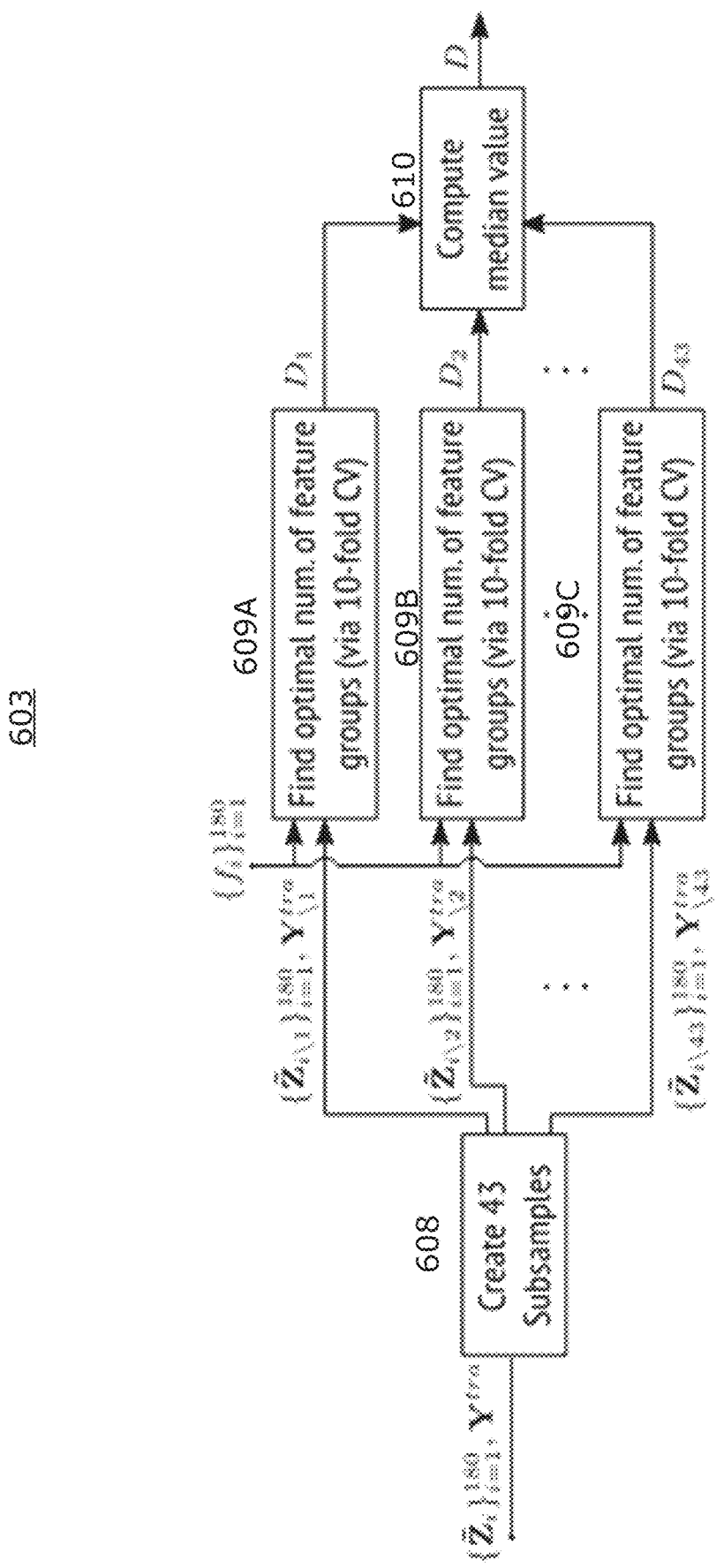
FIG. 6C is a flowchart of a third step of the feature group selection pipeline in FIG. 6A, according to an aspect of the disclosure.

In step 603 (detailed in FIG. 6C), the goal is to find the first D of the ranked feature groups that yield the best performance. This process is carried out in a similar way to the selection of number of PCA components. As illustrated in FIG. 6C, the computer subsamples (step 608) the data matrices 43 times by removing one sample for each subsample, then computes the optimal D value (step 610) per subsample via 10-fold cross-validation (steps 609A-609C) on the inner fold by comparing multiple candidates of the D value. The latter process yields a set of 43 values, $\{D_1, D_2, \ldots, D_{43}\}$, and sets D as the median value of this set. The output of the third block (step 603) is the set of D feature groups with the highest Fisher score, where $\mathcal{Z} = \{\tilde{Z}_{f_1}, \tilde{Z}_{f_2}, \ldots, \tilde{Z}_{f_D}\}$.

Step 604 in FIG. 6A, is the forward feature selection that selects the set of best-performing feature groups $\mathcal{Z}^*$, by initializing it as an empty set and updating it iteratively by adding feature groups from the set $\mathcal{Z}$, and at each iteration removing from $\mathcal{Z}$ the feature group added to $\mathcal{Z}^*$. The quality of a feature group $\tilde{Z}_{f_i} \in \mathcal{Z}$ is measured through the average classification/scoring error:

$$\bar{J}_i = \frac{1}{|\mathcal{Z}|} \sum_{\mathcal{Z}_{f_j} \in \mathcal{Z}} J_{ij} = \frac{1}{|\mathcal{Z}|} \sum_{\mathcal{Z}_{f_j} \in \mathcal{Z}} J(\tilde{Z}_{f_i} \cup \tilde{Z}_{f_j} \cup \mathcal{Z}^*), \quad (3)$$

where $J(\cdot)$ represents a function whose output is classification/scoring error measured via stratified 10-fold cross-validation, using SVM predictors built with the set of feature groups that is passed as its arguments. This process is $\mathcal{O}(D^2)$, as the computer computes $\bar{J}_i$ for all the candidates i=1, . . . , D, and the computation of each $\bar{J}_i$ involves D computations itself. Equation 3 above makes explicit the two criteria employed while selecting features at a given iteration. First, the inclusion of the most up-to-date set of selected features, $\mathcal{Z}^*$, ensures that the feature group $\tilde{Z}_{f_i}$ will not be selected unless it improves performance with respect to already selected feature groups. Second, the computer uses the heuristic that a good feature should achieve good performance when combined with other features. Therefore, the computer evaluates a feature group $\tilde{Z}_{f_i}$ not only in conjunction with the set of selected features $\mathcal{Z}^*$, but also with every other feature in the set of candidates $\mathcal{Z}$, and computes the average performance as shown in equation 3. The best feature of the iteration, $\tilde{Z}_{f_{i^*}}$, is set through $i^* = \arg_i \min \bar{J}_i$. If the of overall performance is improved when $\tilde{Z}_{f_{i^*}}$ is added to the set of selected features $\mathcal{Z}^*$, then $\mathcal{Z}^*$ is updated as $\mathcal{Z}^* \leftarrow \mathcal{Z}^* \cup \tilde{Z}_{f_{i^*}}$, otherwise feature selection is terminated. The algorithmic process described above is outlined below.

```
Initialize: Z* ← ∅, k ← 1, ε* ← 1
While | Z | > 0
    Find best feature group Z_fi* by i* = arg_i min J_i
    If J( Z*∪ Z_fi*) < J( Z*), then Z* ← Z*∪ Z_fi*
        Z ← Z \ Z_fi* k ← k + 1
        ε* ← J( Z*)
    Otherwise
        Break
```

The computer uses the selected feature groups to construct the predictor that performs the ultimate prediction in step 424. The predictor may be an SVM with a linear kernel constructed using the training samples and their labels. Predictors (e.g., classifiers or regressors) other than an SVM with a linear kernel can also be used as long as the number of training samples is adequate. The predictor is trained as follows. Let $\mathcal{Z}^* = \{\tilde{Z}_{f_1^*}, \tilde{Z}_{f_2^*}, \ldots, \tilde{Z}_{f_{D^*}^*}\}$ be the set of selected features where each $\tilde{Z}_{f_i^*}$ represents the PCA-compressed data matrix of the feature group with the index $f_i^*$. That is, $\tilde{Z}_{f_i^*}$ is a matrix whose size is $N^{tra} \times K_{f_i^*}$, where $K_{f_i^*}$ is the number of PCA components and $N^{tra}$ is the number of training samples. The data used to train the predictor is a matrix $X^{tra}$ obtained by concatenating horizontally all the data from the selected feature groups. Therefore, the size of the matrix $X^{tra}$ is $N^{tra} \times (K_{f_1^*} + K_{f_2^*} + \ldots + K_{f_{D^*}^*})$. The parameter that needs to be set for an SVM with linear kernel is the c parameter (e.g., the misclassification penalty). The computer can set this parameter, for example, through grid search; the candidate c values can be $2^1, 2^2, \ldots, 2^6$, and the computer can set c to the value that maximizes 10-fold stratified cross-validation on the training data $X^{tra}$ with the corresponding labels $Y^{tra}$. The computer trains an SVM with a linear kernel using the parameter c and all the training samples, $X^{tra}$ and their corresponding labels $Y^{tra}$. The above-described procedure is applicable to prediction tasks that involve classification or scoring. In the case of classification, an SVM classifier with linear kernel can be used and $Y^{tra}$ can contain categorical labels. In the case of scoring, an SVM regressor with a linear kernel can be used and $Y^{tra}$ can contain numeric (continuous or integer) values.

The LOOCV prediction accuracy for classification in the example dataset with 44 samples was found to be 90.91% (95% CI=78.33 to 97.37; p<0.001; kappa value 0.804) with a balanced accuracy of 89.32%, positive predictive value of 0.93 and negative predictive value of 0.90. The task for this example dataset was to predict ASD group membership (e.g., classification as ASD positive or ASD negative).

The prediction algorithm may also rank the evaluated subject(s) to a level within a group (e.g., mild/severe ASD, Depression, etc.) by scoring the subject(s) on a scale (e.g., 0-10). These scores may be beneficial. For example, medical personnel may use the rankings/scores to initially diagnose a patient, determine treatment, and monitor patient progress. In another example, a matchmaker may use these ranks/scores to match the subject to a potential mate with a similar ranking/score.

The example dataset with 44 samples contains 16 ASD-positive subjects that have an ASD severity score given by the autism clinical experts using a standardized interaction with the ASD-positive subjects, namely the Calibrated Severity Score (CSS) overall score, which is an integer that ranged in 0-10. In an example, the CSS overall scores of those 16 subjects have been predicted by the computer (using an SVM regressor with a linear kernel) via LOOCV. The support vector regression between the CSS overall scores of the experts and the CSS overall scores predicted by the computer was 0.57 and significant (p=0.02). When examining the two components of the overall CSS score, one for social affect and the other for restricted and repetitive behaviors, good convergent and discriminant validity was found in that there was no significant relationship to a 3 minute unstructured dyadic conversation (r=0.00) but there was a significant relationship to the score best capture social communication skills (r=0.58). These results were replicated in an independent adolescent sample with nearly identical statistical findings.

The training and prediction algorithms described above can also be scaled to communicative interactions between more than two participants. For example, there could be a group social setting with multiple interlocutors and multiple subjects. The physical characteristics of each participant would similarly be recorded and analyzed across one or more members of the group. For example, the system could cross-correlate the facial features of participant P1 with the facial features of participants P2, P3, ... PN, and perform the prediction algorithm based on these cross-correlation outputs. This may be beneficial, because participants could exhibit certain traits and behavior in group settings that they may not exhibit in intimate interactions. This may be accomplished by a biometric sensor device with one or more cameras, one or more microphones and the ability to receive wearable sensor data. Similarly, the training and prediction algorithms described above can also be adjusted to for a single participant (e.g., not dyadic or group interactions) by using features computed from the single participant (e.g., the monadic features) rather than dyadic features. In this case, instability during feature selection can be less problematic as the number of features is much smaller (e.g., the 64,800 dyadic features are derived originally from 180 monadic features), and therefore grouping the features to improve stability may not be needed.

Figure 7:
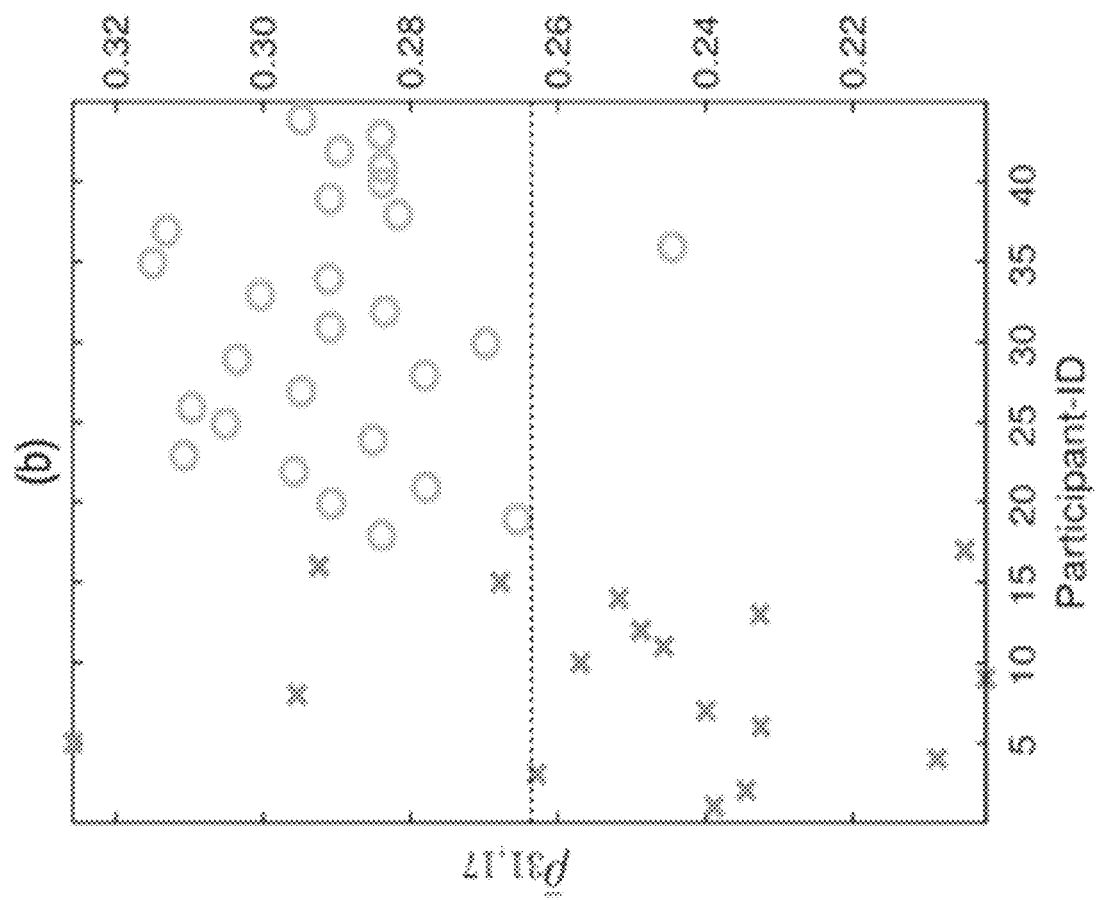
FIG. 7 is an example of prediction results, according to an aspect of the disclosure.
Figure 7:
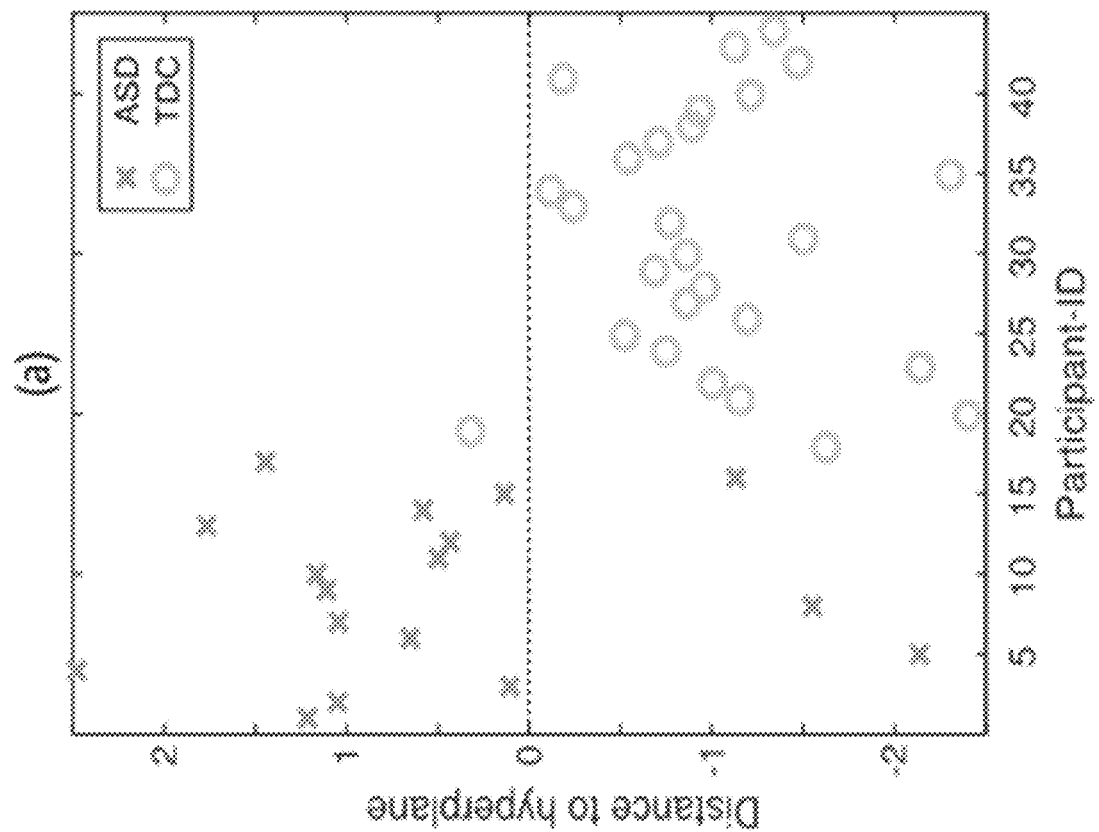

FIG. 7 is an example of prediction results on the example dataset with the 44 samples, according to an aspect of the disclosure. FIG. 7, window (a) shows the distances to an SVM hyperplane for each of the 44 samples in the example dataset. SVM predicts a sample as ASD-positive if the distance is larger than 0, and it predicts as ASD-negative otherwise. The SVM predictor produces a false negative for Participant-5, Participant-8 and Participant-16, and a false positive for Participant-19. FIG. 7, window (b) shows that $\rho_{31,17}$ emerges as the only dyadic feature of $\rho_{17}$ that significantly correlates with the SVM distances shown in FIG. 7, window (a). The dashed line in FIG. 7, window (b) shows a value that optimally separates the groups. Some other features correlate strongly with $\rho_{17}$ and thus can also be used alone or in combinations for very accurate predictions.

In addition to the methods described above, there are various other methods for using the biometric sensor device to analyze and classify participants. These include but are not limited to analyzing natural conversational utterances, analyzing acoustic properties of speech, determining how classification changes over long periods of time and with different age groups, and analyzing imitation of participants. Some of these examples are described in more detail below.

Natural Conversational Utterances

The earliest descriptions of ASD include mention of atypical speech patterns, including unusual prosody. Although phonetic properties of speech have been explored in ASD, most prior research samples were either elicited in a highly structured context (e.g., reading sentences or word lists) or drawn from semi-structured clinical interviews with an autism expert (i.e., ADOS evaluations). While valuable, these studies produce results that may not generalize to the everyday conversations that really matter for children on the autism spectrum. In one study, machine learning classification approach to utterances produced by children during natural interactions with a naïve conversational partner was performed. This included automatically measuring phonetic features of utterances in the natural conversations of children with and without ASD, and developing a machine learning classifier to predict, for each utterance, the diagnostic category of the speaker.

In one example, using the biometric sensor device, seventy children with the ASD group (N=35 ASD, 13 of which were females) or typically developing (TD) (N=35 TD, 11 of which were females), matched on IQ (ASD: 105; TD: 107; t=−0.53, p=0.6) and age (ASD: 11.42; TD: 10.57; t=1.33, p=0.19), completed a 5-minute "get-to-know-you" conversation with a novel confederate (N=22 confederates, 19 of which were females). Thirty two intensity and spectral features were extracted from each utterance using. To avoid pitch-halving and -doubling errors, the pitch-tracker was run twice, once to estimate the modal pitch range of each speaker and once to pitch-track within the obtained speaker-specific pitch range. Pitch values were normalized from Hz to semitones using the 5th percentile of each speaker as the base. A support vector machine was trained with a radial basis function kernel and leave-one-group-out cross-validation, where one group means all utterances of one speaker. All features were scaled.

As a result, the classifier correctly identified the diagnostic category of each utterance 73.46% of the time with 70.36% precision, 76.47% recall, 73.6% AUC, and an F1-score of 73.29%. The performance of the model is comparable to previous studies that used phonetic features only. The accuracy of the classifier is high given that the data was drawn from natural conversations, which tend to be messier and more variable than other types of data.

This suggests that acoustic features of natural conversation are useful for distinguishing utterances produced by children with ASD vs. utterances from typically developing children. In an additional step, a second phase of machine learning, with the goal of predicting individual children's diagnostic status using more sophisticated algorithms, feature selection methods, and an expanded feature set (e.g., frequency of non-speech vocalizations, filled pauses) may be executed.

Acoustic Properties of Speech

Behavioral heterogeneity is a persistent challenge for researchers and clinicians aiming to develop evidence-based social communication interventions for children with ASD, and to pinpoint the condition's biological basis. Even after attempting to manufacture homogeneity by restricting variables such as age and IQ within experimental groups, children with ASD often still behave differently across contexts. In one study, latent classes of 'ASD-like' speech patterns (using acoustic properties from a larger machine learning effort to classify utterances as 'ASD' or typically developing 'TD') are analyzed over the course of a naturalistic 5-minute conversation in children with ASD, with the goal of identifying (more) homogeneous subgroups. This tests whether patterns of 'ASD'-like utterances distinguish subgroups of children with ASD over the course of a short, naturalistic conversation with a friendly stranger.

In one example, using the biometric sensor device, language samples from 35 verbally fluent children with ASD were drawn from an unstructured 5-minute 'get-to-know-you' conversation with a novel confederate who was not an autism expert. All children had IQ estimates in the average range (>75), and were aged 7-16.99 years. Children produced a total of 2,408 useable utterances (mean=68.8 utterances each). Each utterance was classified as 'ASD' or 'TD' using a machine learning classifier developed on the acoustic properties of speech produced by a larger sample that included both diagnostic groups. Latent class linear mixed models modeled the number of 'ASD'-like utterances produced over the course of the conversation (~1-minute windows), and latent class member characteristics were compared using simple linear models.

As a result, a 2-class model provided the best fit for the data (as compared to a 3- or 4-class model) and revealed evidence of homogeneous subgroups with (1) Decreasing (N=8) or (2) Increasing (N=27) rates of ASD-like speech utterances over the course of the conversation. Intercepts differed significantly from one another (coefficient: −2.41, Wald test=−3.02, p=0.003), as did slopes (1: Coefficient=−0.55, Wald test=−3.88, p=0.0001; 2: Coefficient=0.42, Wald test=5.50, p=0.0000). Class members did not differ on age, sex ratio, nonverbal IQ estimates, calibrated severity scores, word count, average turn length, or the number of utterances produced at the group level, but did differ on verbal IQ scores (Decreasing>Increasing; estimate=−13.81, t=−3.19, p=0.003).

Thus, machine-learning classification at the utterance level renders it possible to parse heterogeneous samples into more homogeneous subgroups that dynamically change over the course of a conversation. In this exploratory study, two subgroups of children that sound more or less 'ASD-like' over time were found. Interestingly, children with higher verbal IQ estimates produced progressively fewer utterances classified as 'ASD-like', as compared to children with lower verbal IQ estimates, despite similar autism symptom severity. An expanded sample could also include language-based analyses in each class. This 'profiling' approach holds promise for identifying subgroups that benefit from specific interventions and stands to advance the goal of personalized medicine.

Machine Learning Through the Ages

The majority of children with ASD are verbally fluent, and information gathered from brief natural language samples could facilitate remote screening while generating ecologically valid social communication profiles to inform personalized treatment planning. A variety of linguistic features produced by participants with ASD and their conversational partners are useful predictors of diagnostic status and/or symptom severity, including prosody, turn-taking rates, and word choice.

In general, machine learning may be applied to language features extracted from transcripts of naturalistic conversations, with the goals of (1) classifying participants as ASD or typically developing, and (2) comparing classification accuracy and predictive features between a child sample, an adolescent sample, and a collapsed sample that includes all participants.

In one study, using the biometric sensor device, eighty-five matched participants participated in two 3-minute semi-structured "get to know you" conversations with two previously unknown confederates who were not autism experts. In the first conversation, the confederate is trained to act interested in the conversation, and in the second, bored. Transcripts were analyzed resulting in 121 extracted features for participants and confederates in each condition, as well as the difference between conditions. The machine learning pipeline included a logistic regression classifier trained with participant and/or confederate features within a leave-one-out-cross-validation loop. Cross-validated classification accuracy was measured within children and adolescent samples separately, as well as across the entire age range; accuracy was compared using McNemar's test. Conversational features with non-zero coefficients in the classifier were identified as top predictors of diagnostic status.

As a result, diagnostic classification accuracy was high in both age groups: 89% in adolescents and 76% in younger children. Accuracy dropped to 66% (p<0.015) when the entire age range was classified within a single model, suggesting that optimal classification models may differ by age group. The most accurate classification model was driven by participant-level features for children and by confederate-level features for adolescents. For children, top predictive features included participant pronoun use, intra-turn pause duration, and "friend"-category words. For adolescents, top predictive features in the most parsimonious model included confederate word-level "authenticity" and negations.

This study showed that (1) features derived from naturalistic conversations with non-expert interlocutors can be used for diagnostic classification, and (2) top classification features change over the course of development. Using machine learning to extract clinically-relevant dimensions from short, naturalistic conversation samples with naïve confederates may provide a new path toward rapid improvements in remote screening, characterization, and developing yardsticks for measuring treatment response.

Imitation and Motor Learning

Meta-analysis indicates that imitation differences are strongly and specifically associated with ASD. While differences are robust across tasks, how imitation is operationalized within studies moderates whether differences are detected (e.g. measuring form distinguishes ASD from non-ASD better than simply measuring end states). Accurately measuring the form of actions as they unfold requires tools that are spatially and temporally granular. In one example, an automated computer vision approach is applied to measure imitation, compare a scalable, open-source motion-tracking program against an established but more resource-intensive system.

In one study, participants included 21 children with ASD and 18 typically developing children (TDC). Children imitated in real time a 2.5-minute video of a man making a sequence of body movements. The task was completed twice, separated by another brief task. The biometric tree sensor collected front-facing whole body video at 30 frames/second. Joint movements were digitally tracked in coordinate space. Imitation performance was quantified through windowed cross-correlations (4-second sliding windows) on child joint coordinates relative to joint coordinates from the stimulus video (ground truth).

The study showed that there were significant group by timepoint interactions for movement of both wrists of the participant using, with large effect sizes [left: p=0.02, $\eta_p^2$=0.15; right: p=0.01, $\eta_p^2$=0.16]. TDCs significantly outperformed the ASD group for both wrists at Time 2 [left: p=0.002, d=1.07; right: p=0.003, d=1.03], but not Time 1 [left: p=0.11, d=0.53; right: p=0.17, d=0.46]. TDC performance was significantly higher at Time 2 than Time 1 [left: p=0.03, d=0.54; right: p=0.03, d=0.54], whereas the ASD group did not differ significantly across time points [left: p=0.15, d=−0.34; right: p=0.11, d=−0.40], showing a lack of improvement with practice in ASD. Neither interaction terms nor timepoint effects reached significance for either wrist.

Results are consistent with known imitation differences in ASD. Specifically, the results are suggestive of impaired motor learning. This approach benefits due to the acquisition of raw movement data, rather than reliance on human raters. Such granular measurement should improve imitation assessment, particularly of change over time (e.g., treatment outcomes). 3D motion tracking outperformed 2D tracking; the latter yielded higher levels of noise in movement representations.

In another study, based on the same sample used in the imitation study described above, imitation was tracked using computer vision to create skeletons for the subjects (e.g., at each video frame). The skeletons were defined by 20 joint markers (e.g., more than just the wrist used in the imitation study just described). Imitation error was coded as the Euclidian distance between each of the subject's 20 joints, and ground truth from the human who modeled the movements which were being imitated by the subject. A second, independent source of error was calculated as the sum of the subject's time lag at each video frame from the ground truth model. Both error types significantly distinguished the group with ASD from the matched typical control group (p's<0.01). Next, support vector machine learning was used with on this group of 21 youth with ASD and 18 TDs, matched on Age, Sex and IQ using both positional accuracy data and timing accuracy (lag). Using a nested leave one out cross validation (LOOCV) approach to guard against over fitting the data, overall accuracy in predicting an ASD vs TD was 85% (sensitivity=0.81, positive predictive value=0.89, specificity=0.89, and negative predictive value=0.80). All results were significant at p<0.05. Nearly all of the same features appeared in each fold of the LOOCV, suggesting a stable prediction model.

The steps in FIGS. 4A-4C and 6A-6C may be performed by the controller upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. In one example, data are encrypted when written to memory, which is beneficial for use in any setting where privacy concerns such as protected health information is concerned. Any of the functionality performed by the controller described herein, such as the steps in FIGS. 4A-4C and 6A-6C, may be implemented in software code or instructions which are tangibly stored on a tangible computer readable medium. Upon loading and executing such software code or instructions by the controller, the controller may perform any of the functionality of the controller described herein, including the steps in FIGS. 4A-4C and 6A-6C described herein.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

The term "component" when referring to the biometric sensor device may comprise any device internal or external to the biometric sensor device. The component, for example, may be a processor, a sensor, a camera, a wire, etc.

The physical characteristics include but are not limited to facial position/movement (e.g., movement of eyes, lips, etc.), body movement (e.g., movement of limbs, head, etc.), vocalization (e.g., speech content, speech acoustics, etc.), electrophysiological signals (e.g., ECG signals, etc.).

The term "facial landmark" refers to portions of the participant's face including but not limited to the eyes, lips, nose, chin, head, and ears.

The term "body landmark" refers to portions of the participant's body including but not limited to arms, legs, head, shoulders and torso.

The term "vocal landmark" refers to features of the participant's vocalization including but not limited to speech content, utterances, and acoustic properties.

The term "participant" refers to any person participating in the session recorded by the biometric sensor device. This participant may be the subject to be evaluated (e.g., classified/scored/ranked), or an interlocutor that may or may not be subject to evaluation.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. A biometric sensor device system comprising:
   a biometric sensor device; and
   a prediction computer,
   the biometric sensor device including:
      at least one camera, and
      a biometric sensor device processor configured to:
         record a time synchronized communicative interaction between participants, by controlling at least one camera to record the participants over a time period, and
         transfer the recorded communicative interaction to the prediction computer,
   the prediction computer including:
      a prediction computer processor configured to:
         extract, from the recorded communicative interaction, a physical characteristic of each of the participants over the time period,
         compare, the physical characteristic of at least one of the participants with the physical characteristic of at least another one of the participants over the time period, and
         classify or score at least one of the participants according to a predetermined classification or dimensional scoring scheme based on the comparison.

2. The biometric sensor device system of claim 1,
   wherein the compared physical characteristic of the participants includes at least one of the movement of facial landmarks of the participants, movement of body landmarks of the participants, vocal landmarks of the participants including language content or acoustic properties or electrophysiological signals of the participants, which are time synchronized with each other, and
   wherein the prediction computer processor is further configured to:
      record the physical characteristics over a period of time during communicative interaction,
      compare the physical characteristics, and
      classify and/or score at least one of the participants according to a predetermined classification or scoring scheme based on the comparison.

3. The biometric sensor device system of claim 2,
   wherein the prediction computer processor is further configured to:
      compare the physical characteristics by correlating the physical characteristics of at least one of the participants with the physical characteristics of at least another one of the participants, and
      classify and/or score at least one of the participants according to a predetermined classification and/or scoring scheme by analyzing the correlations that are known to correspond to the predetermined classification and/or score.

4. The biometric sensor device system of claim 3,
   wherein the prediction computer processor is further configured to:
      correlate each of the physical characteristics of the participants by overlaying a first signal representative of the physical characteristics of at least one of the participants with a second signal representative of the physical characteristics of at least another one of the participants, and cross-correlating the overlapped signals in a sequence of time windows to determine a maximum correlation between the overlapped signals at each time window.

5. The biometric sensor device system of claim 4
   wherein, during a training process, the prediction computer processor is further configured to select a plurality of the correlations that maximize classification or scoring accuracy when compared to known classification or scoring results.

6. The biometric sensor device system of claim 5,
   wherein, during the training process, the prediction computer processor is further configured to select the plurality of the correlations by grouping the physical characteristics into multiple groups, determining the classification or scoring accuracy of each group, and selecting the groups that yield the highest classification or scoring accuracy.

7. The biometric sensor device system of claim 6,
   wherein the prediction computer processor is further configured to classify or score at least one of the participants according to a predetermined classification or scoring scheme by choosing correlations or feature groups determined during the training process and analyzing the chosen correlations determined during the prediction process.

8. The biometric sensor device system of claim 1,
   wherein at least one of the participants is an interlocutor and at least another one of the participants is a subject of a neurological or psychiatric disorder test, and
   wherein the prediction computer processor is further configured to classify at least one of the participants as either positive or negative for the neurological disorder or psychiatric disorder.

9. The biometric sensor device system of claim 1,
   wherein at least one of the participants is a subject of a psychological and/or psychosocial test, and
   wherein the prediction computer processor is further configured to classify at least one of the subjects as either positive or negative for the psychological test or provide a ranking or score for at least one of the subjects on the psychosocial test.

10. The biometric sensor device system of claim 1,
    wherein the prediction computer processor is further configured to use other physical characteristics of at least one of the participants to perform the prediction, the other physical characteristics including at least one of movement of body parts other than the face, audio signals including lexical or acoustic properties of speech, or electrophysiological signals.

11. A biometric sensor device comprising:
   at least one camera; and
   a processor configured to:
   record a time synchronized communicative interaction between participants, by controlling the at least one camera to record the participants over a time period,
   extract, from the recorded communicative interaction, a physical characteristic of each of the participants over the time period,
   compare, the physical characteristic of at least one of the participants with the physical characteristic of at least another one of the participants over the time period, and
   classify or score at least one of the participants according to a predetermined classification or dimensional scoring scheme based on the comparison.

12. The biometric sensor device of claim 11, further comprising:
   an adjustable mount for at least one camera,
   wherein the adjustable mount is configured to direct the at least one camera towards the participants.

13. The biometric sensor device of claim 11, further comprising at least one of:
   a wireless transceiver to transfer the recorded communicative interaction to a prediction computer; or
   a removable memory device to transfer the recorded communicative interaction to the prediction computer.

14. The biometric sensor device of claim 11, further comprising:
   a base to seat the biometric sensor device on a table between participants;
   a suspension system to suspend the biometric sensor device above the participants; or
   an adjustable stand to seat the biometric sensor device on a floor between the participants.

15. The biometric sensor device of claim 11, further comprising:
   directional microphones to record audio of the participants during the communicative interaction, the audio being time synchronized with video from the at least one camera,
   wherein the compared physical characteristic of the participants includes movement of the participants captured by the at least one camera and the language content or acoustic properties of the participants captured by the directional microphones.

16. The biometric sensor device of claim 15, further comprising:
   a wireless transceiver or an input port to receive data from a sensor worn by at least one of the participants during the communicative interaction, the sensor data being time synchronized with the video from the at least one camera and the audio from the directional microphones,
   wherein the compared physical characteristic of the participants includes the movement of the participants captured by the at least one camera, the language content or acoustic properties of the participants captured by the directional microphones, and the data from the sensor worn by the at least one of the participants.

17. The biometric sensor device of claim 11,
   wherein the sensor includes at least one of an accelerometer, gyroscope, or electrophysiological probes to respectively record time synchronized body movement and orientation signals and electrical signals of the participants.

18. The biometric sensor device of claim 11,
   wherein the processor is further configured to:
   perform prediction for at least one of the participants according to a predetermined classification or scoring scheme based on the comparison.

19. The biometric sensor device of claim 18,
   wherein the processor is further configured to:
   record movement of time synchronized facial or body landmarks or vocal landmarks or vocal content or electrophysiological body signals over a period of time during the communicative interaction,
   compare the movement of the time synchronized facial or body landmarks or the vocal landmarks or vocal content or electrophysiological body signals, and
   classify or score at least one of the participants according to a predetermined classification or scoring scheme based on the comparison of the movement of the time synchronized facial or body landmarks or the vocal landmarks or vocal content or electrophysiological body signals.

20. The biometric sensor device of claim 19,
   wherein the processor is further configured to:
   compare the movement of the time synchronized facial or body landmarks or the vocal landmarks by correlating each of the time synchronized facial or body landmarks or the vocal landmarks of at least one of the participants with each of the time synchronized facial or body landmarks or the vocal landmarks of at least another one of the participant, and
   classify or score at least one of the participants into the predetermined classification by analyzing the correlations that are known to correspond to the predetermined classification or scoring results.

* * * * *